United States Patent
Kang et al.

(10) Patent No.: US 12,350,295 B2
(45) Date of Patent: Jul. 8, 2025

(54) COMPLEX FOR PROMOTING CARTILAGE DIFFERENTIATION COMPRISING CARTILAGE CELL-FREE CRUSH AND STEM CELL AND USE THEREOF

(71) Applicant: KANGSTEM BIOTECH CO., LTD., Seoul (KR)

(72) Inventors: Kyung Sun Kang, Seoul (KR); Seung Hee Lee, Seoul (KR); Jong Chan Ahn, Seoul (KR); Mi Jin Kim, Seoul (KR)

(73) Assignee: KANGSTEM BIOTECH CO., LTD., Seoul (KR)

( * ) Notice: Subject to any disclaimer, the term of this patent is extended or adjusted under 35 U.S.C. 154(b) by 791 days.

(21) Appl. No.: 16/315,377

(22) PCT Filed: Jul. 4, 2017

(86) PCT No.: PCT/KR2017/007077
§ 371 (c)(1),
(2) Date: Jul. 16, 2019

(87) PCT Pub. No.: WO2018/008941
PCT Pub. Date: Jan. 11, 2018

(65) Prior Publication Data
US 2019/0365820 A1    Dec. 5, 2019

(30) Foreign Application Priority Data
Jul. 4, 2016    (KR) ........................ 10-2016-0084171

(51) Int. Cl.
*A61P 19/02*    (2006.01)
*A61K 35/32*    (2015.01)
(Continued)

(52) U.S. Cl.
CPC .............. *A61K 35/32* (2013.01); *A61K 35/51* (2013.01); *A61K 35/545* (2013.01);
(Continued)

(58) Field of Classification Search
None
See application file for complete search history.

(56) References Cited

U.S. PATENT DOCUMENTS

| | | | | |
|---|---|---|---|---|
| 4,473,551 A | * | 9/1984 | Schinitsky | A61K 35/32 424/548 |
| 2009/0319045 A1 | * | 12/2009 | Truncale | A61L 27/48 623/23.73 |

(Continued)

FOREIGN PATENT DOCUMENTS

| JP | 101569198 B1 | 11/2015 |
|---|---|---|
| WO | 2012126824 A1 | 9/2012 |

(Continued)

OTHER PUBLICATIONS

Benders et al., Trends in Biotechnology, Mar. 2013, vol. 31, No. 3, pp. 169-176 (Year: 2013).*

(Continued)

*Primary Examiner* — Evelyn Y Pyla
(74) *Attorney, Agent, or Firm* — Edwin S. Flores; Daniel J. Chalker; Chalker Flores, LLP

(57) ABSTRACT

The present invention relates to a complex for promoting cartilage differentiation comprising stem cells or a culture thereof and a cartilage cell-free crush, a method for fabricating cartilage by using the complex, cartilage fabricated via the method, a pharmaceutical composition comprising the complex for preventing or treating arthropathy, a method for preventing or treating arthropathy using the composition, a composition for inducing cartilage cell differentiation comprising the prepared cartilage cells, and a method for fabricating cartilage using the prepared cartilage cells. The complex for promoting cartilage differentiation comprising the stem cells or the culture thereof and the cartilage cell-free crush provided in the present invention is not only differentiated into cartilage cells without side effects even in (Continued)

vivo, but also promotes differentiation of inherent stem cells in vivo into cartilage cells via a paracrine effect exhibited in the differentiated cartilage cells to effectively regenerate the damaged cartilage, and thus the complex may be widely used for treatment of arthropathy involving the cartilage damage.

5 Claims, 14 Drawing Sheets

Specification includes a Sequence Listing.

(51) Int. Cl.
| | | |
|---|---|---|
| *A61K 35/51* | (2015.01) | |
| *A61K 35/545* | (2015.01) | |
| *C12N 5/077* | (2010.01) | |
| *C12N 5/0775* | (2010.01) | |

(52) U.S. Cl.
CPC ......... *C12N 5/0655* (2013.01); *C12N 5/0665* (2013.01); *C12N 2506/1369* (2013.01)

(56) References Cited

U.S. PATENT DOCUMENTS

| | | |
|---|---|---|
| 2010/0003754 A1 | 1/2010 | Briest et al. |
| 2010/0104641 A1 | 4/2010 | Thie et al. |
| 2010/0303773 A1* | 12/2010 | Yang ................. A61K 38/1709 435/375 |
| 2014/0024115 A1* | 1/2014 | Bogdansky .......... C12N 5/0667 435/395 |

FOREIGN PATENT DOCUMENTS

| | | |
|---|---|---|
| WO | 2015053739 A1 | 4/2015 |
| WO | WO-2015048317 A1 * | 4/2015 ............. A61K 35/32 |

OTHER PUBLICATIONS

Huang et al., Cells Tissues Organs, vol. 201: 354-365 (2015), Abstract (Year: 2015).*
Lin et al., Oncotarget, (2016) vol. 7, No. 11, pp. 12121-12136 (Year: 2016).*
Bauerfeind Medical: Knee osteoarthritis (Gonarthosis), 9 pages, retrieved from the internet:https://bauerfeind.ca/blogs/arthritis-arthrosis/knee-osteoarthritis-gonarthosis?locale=en (Year: 2022).*
Centano et al. Pain Physician 2008; 11:3:343-353 (Year: 2008).*
Kern et al., Stem Cells 2006; 24:1294-1301 (Year: 2006).*
Zhang et al., Tissue Engineering: Part B, vol. 20, No. 6, 2014, pp. 655-668 (Year: 2014).*
International Search Report (PCT/KR2017/007077) ISA/KR dated Oct. 26, 2017.
Sutherland, Amanda J. et al. "Decellularized Cartilage May Be a Chondroinductive Material for Osteochondral Tissue Engineering" PLoS ONE 10(5):e0121966, doi:10.1371/journal.pone.0121966 (May 12, 2015).
Talakoob, Setareh et al. "Capability of Cartilage Extract to In Vitro Differentiation of Rat Mesenchymal Stem Cells (MSCs) to Chondrocyte Lineage" Int J Mol Cell Med Winter 2015; vol. 4 No 1; 9-21.
Tang, Xinjie et al. "Differentiation of bone marrow-derived mesenchymal stem cells into chondrocytes using chondrocyte extract" Molecular Medicine Reports 6: 745-749, 2012.
Extended European Search Report [EP17824497.6] dated Jan. 24, 2020.
Chang, Chih-Hung et al. "Human acellular cartilage matrix powders as s biological scaffold for cartilage tissue engineering with synovium-derived mesenchymal stem cells" Journal of Biomedical Materials Research, Part A, vol. 102, Issue 7, Jul. 31, 2013, 23 pages.
Hubka, Kelsea M. et al. "Enhancing Chondrogenic Phenotype for Cartilage Tissue Engineering: Monoculture and Coculture of Articular Stem Cells" Tissue Engineering, Part B, vol. 20, No. 6, 2014, 641-654.
Nagura, Issei et al. "Chondrogenic Potential of Human Rotator Cuff Derived Cells" Japan Shoulder Society, 2011, vol. 35, No. 3, pp. 829-832.
Shin, Yoo Seob et al. "Tissue-Engineered Tracheal Reconstruction Using Mesenchymal Stem Cells Seeded in a Porcine Cartilage Powder Scaffold" Annals of Biomedical Engineering, vol. 43, No. 4, Apr. 2015, pp. 1003-1013.
Sutherland, Amanda J. et al., "Decellularized Cartilage May Be a Chondroinductive Material for Osteochondral Tissue Engineering" PLOS One, May 12, 2015, vol. 10, No. 5, pp. 1-13.
Yin, Heyong et al. "Induction of mesenchymal stem cell chondrogenic differentiation and functional cartilage microtissue formation for in vivo cartilage regeneration by cartilage extracellular matrix-derived particles" Acta Biomaterialia, 2016, vol. 33, pp. 96-109.

* cited by examiner

SEQUENCE LISTING

```
<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: Synthetic primer

<400> SEQUENCE: 1
```
ctgcattcca cgaagctaac ct                                              22

<210> SEQ ID NO 2
<211> LENGTH: 19
<212> TYPE: DNA
<213> ORGANISM: Artificial Sequence
<220> FEATURE:
<223> OTHER INFORMATION: Synthetic primer

<400> SEQUENCE: 2
gacgcctcgc cttcttgaa                                                  19

<210> SEQ ID NO 3
<211> LENGTH: 22
<212> TYPE: DNA
<213> ORGANISM: Artificial Sequence
<220> FEATURE:
<223> OTHER INFORMATION: Synthetic primer

<400> SEQUENCE: 3
ctactggatt gaccccaacc aa                                              22

<210> SEQ ID NO 4
<211> LENGTH: 22
<212> TYPE: DNA
<213> ORGANISM: Artificial Sequence
<220> FEATURE:
<223> OTHER INFORMATION: Synthetic primer

<400> SEQUENCE: 4
tccatgttgc agaaaacctt ca                                              22

<210> SEQ ID NO 5
<211> LENGTH: 21
<212> TYPE: DNA
<213> ORGANISM: Artificial Sequence
<220> FEATURE:
<223> OTHER INFORMATION: Synthetic primer

<400> SEQUENCE: 5
gacttctgaa cgagagcgag a                                               21

<210> SEQ ID NO 6
<211> LENGTH: 21
<212> TYPE: DNA
<213> ORGANISM: Artificial Sequence
<220> FEATURE:
<223> OTHER INFORMATION: Synthetic primer

<400> SEQUENCE: 6
ccgttcttca ccgacttcct c                                               21

<210> SEQ ID NO 7
<211> LENGTH: 19
<212> TYPE: DNA
<213> ORGANISM: Artificial Sequence
<220> FEATURE:
<223> OTHER INFORMATION: Synthetic primer

<400> SEQUENCE: 7
caggaagggc cacgacaaa                                                  19

<210> SEQ ID NO 8
<211> LENGTH: 18
<212> TYPE: DNA
<213> ORGANISM: Artificial Sequence

```
<220> FEATURE:
<223> OTHER INFORMATION: Synthetic primer

<400> SEQUENCE: 8
ctgcggcaca agggattg                                                  18

<210> SEQ ID NO 9
<211> LENGTH: 24
<212> TYPE: DNA
<213> ORGANISM: Artificial Sequence
<220> FEATURE:
<223> OTHER INFORMATION: Synthetic primer

<400> SEQUENCE: 9
ctatgaccaa taggaagagc aacc                                           24

<210> SEQ ID NO 10
<211> LENGTH: 23
<212> TYPE: DNA
<213> ORGANISM: Artificial Sequence
<220> FEATURE:
<223> OTHER INFORMATION: Synthetic primer

<400> SEQUENCE: 10
gcagagtata tgaccaggtg gaa                                            23

<210> SEQ ID NO 11
<211> LENGTH: 24
<212> TYPE: DNA
<213> ORGANISM: Artificial Sequence
<220> FEATURE:
<223> OTHER INFORMATION: Synthetic primer

<400> SEQUENCE: 11
gctatgctgc caattactgt gatg                                           24

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
tgcattcatg tgtgcgttga                                                20
```

COMPLEX FOR PROMOTING CARTILAGE DIFFERENTIATION COMPRISING CARTILAGE CELL-FREE CRUSH AND STEM CELL AND USE THEREOF

CROSS-REFERENCE TO RELATED APPLICATIONS

This application is the National Stage of International Application No. PCT/KR2017/007077, filed on Jul. 4, 2017, claiming the priority of KR 10-2016-0084171, filed on Jul. 4, 2016, the content of each of which is incorporated by reference herein.

INCORPORATION-BY-REFERENCE OF MATERIALS FILED ON COMPACT DISC

The present application includes a Sequence Listing which has been submitted in ASCII format via EFS-Web and is hereby incorporated by reference in its entirety. Said ASCII copy, created on Jan. 6, 2019, is named HANO1018US_SeqList.txt and is 3 kilobytes in size.

TECHNICAL FIELD

The present invention relates to a complex for promoting cartilage differentiation comprising a cartilage cell-free crush and stem cells and a use thereof, and more particularly, to a complex for promoting cartilage differentiation comprising stem cells or a culture thereof and a cartilage cell-free crush, a method for fabricating cartilage by using the complex, cartilage fabricated by the method, a pharmaceutical composition comprising the complex for preventing or treating arthropathy, a method for preventing or treating arthropathy by using the composition, a composition for inducing cartilage cell differentiation comprising the prepared cartilage cells, and a method for fabricating cartilage by using the prepared cartilage cells.

BACKGROUND ART

Arthropathy is a term collectively referring to diseases involving analgia and dysarthrosis, and is classified as a neurotrophic disease of the joints. Usually, arthropathy comprises polyarthrosis, coxarthrosis, gonarthrosis, spondyloarthropathy, and the like, and may involve cartilage damage or cartilage dysfunction, and since most joint diseases involve inflammation, it is known that the joint diseases can progress to arthritis.

Arthritis derived from arthropathy is a frequently occurring disease having the highest prevalence rate among diseases suffered by humans, and degenerative arthritis, included therein, is a representative geriatric disease having an incidence rate of 70% to 80% in the population over 65 years old, and nearly 100% in those over 75 years old. At present, in Korea, more than 10% of the total population suffers from degenerative arthritis, and this prevalence rate is quickly increasing due to the rapid aging of Korean society. Recently, degenerative arthritis has even occurred in many young people, and it is also estimated that there are more than about 500 million people with degenerative arthritis worldwide. In addition, as the duration of human societal activity increases and the average life span of human beings also grows longer, degenerative arthritis occupies an important place which must be urgently overcome in terms of the quality of human life.

Degenerative arthritis is mainly caused by damage to the cartilage tissue located in the knee joint. The cartilage cells contained in the cartilage tissue serve to synthesize and secrete a matrix such as collagen and proteoglycan, and also decompose the same at an appropriate rate, which is required for maintaining the normal function of the cartilage tissue, and plays an essential role in maintaining the functional homeostasis of an articular cartilage tissue. Various studies have been conducted to treat such arthritic symptoms. For example, U.S. Pat. No. 6,025,334 discloses an agent for treating arthritis comprising a shark cartilage extract, and Korean Patent Registration No. 1569168 discloses a technique of treating rheumatoid arthritis using placental stem cells or umbilical cord stem cells. However, since the shark cartilage extract has an effect of suppressing cartilage damage and does not exhibit the effect of treating or regenerating damaged cartilage, and the stem cells may be differentiated into cells other than cartilage cells in joint tissue, there is a drawback in that side effects may occur. Accordingly, research has been actively conducted to develop a method of treating or regenerating damaged cartilage without side effects.

DISCLOSURE

Technical Problem

The present inventors have conducted intensive research to develop a method for more effectively treating arthropathy accompanied by cartilage damage. As a result, the present inventors confirmed that when stem cells or a culture thereof and a cartilage cell-free crush are complexly administered to the damaged cartilage, the stem cells are necessarily differentiated into cartilage cells to regenerate a cartilage tissue or promote regeneration of the damaged cartilage due to a paracrine effect around the administration site and more effectively treat the arthropathy, and thereby completing the present invention.

Technical Solution

One object of the present invention is to provide a complex comprising stem cells or a culture thereof and a cartilage cell-free crush for promoting cartilage differentiation.

Another object of the present invention is to provide a method for fabricating cartilage using the complex.

Yet another object of the present invention is to provide cartilage fabricated via the method.

Still another object of the present invention is to provide a pharmaceutical composition for preventing or treating arthropathy comprising the complex.

Still yet another object of the present invention is to provide a method for preventing or treating arthropathy using the composition.

Still yet another object of the present invention is to provide a composition for inducing cartilage cell differentiation comprising the fabricated cartilage cells.

Still yet another object of the present invention is to provide a method for fabricating cartilage using the fabricated cartilage cells.

Still yet another object of the present invention is to provide a use of a complex for promoting cartilage differentiation comprising stem cells or a culture thereof and a cartilage cell-free crush for fabricating cartilage.

Still yet another object of the present invention is to provide a use of a complex for promoting cartilage differentiation comprising stem cells or a culture thereof and a cartilage cell-free crush for preventing or treating arthropathy.

Advantageous Effects

The complex for promoting cartilage differentiation comprising the stem cells or the culture thereof and the cartilage cell-free crush provided in the present invention is not only differentiated into cartilage cells without side effects even in vivo, but also promotes differentiation of inherent stem cells in vivo into cartilage cells via a paracrine effect exhibited in the differentiated cartilage cells to effectively regenerate damaged cartilage, and thus the complex may be widely used for treatment of arthropathy involving cartilage damage.

BEST MODE FOR INVENTION

Figure 1A:
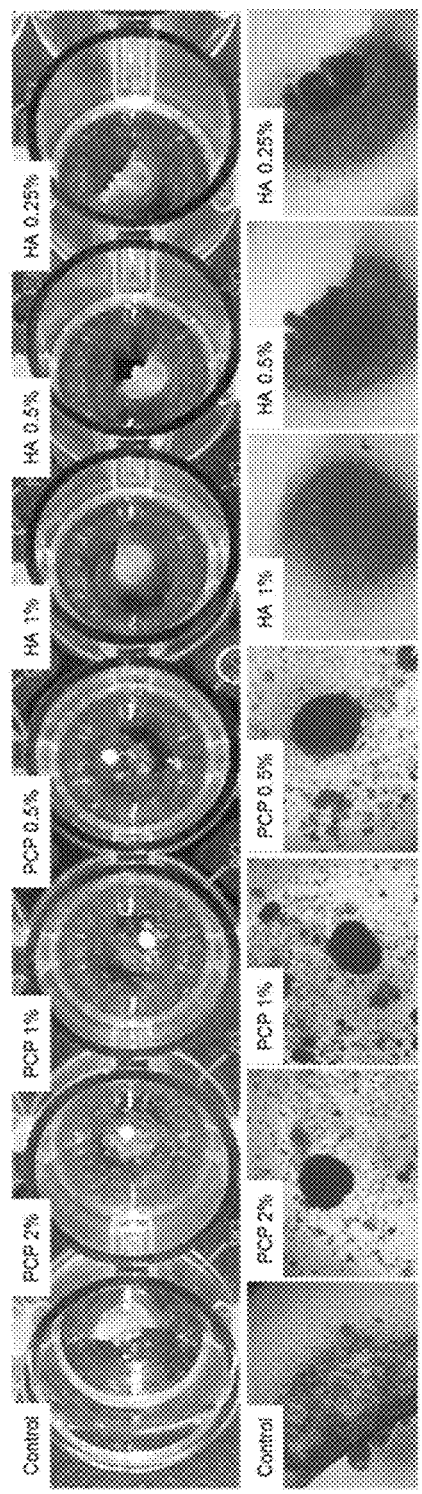
FIG. 1A is a micrograph showing results of evaluating a cartilage differentiation level of human umbilical cord blood-derived mesenchymal stem cells (UCB-MSC) according to types and treatment concentrations of a cartilage differentiation inducer.

The present inventors have focused on stem cells while carrying out various studies in order to develop a method for more effectively treating arthropathy. Since most types of arthropathy are caused by damage to the cartilage located in the joints, it is assumed that if the damaged cartilage may be restored or regenerated, the arthropathy may be effectively treated, and thus studies were conducted to find a method for regenerating the cartilage using stem cells. However, while various methods of differentiating stem cells into cartilage cells have been known under in vitro conditions, under in vivo conditions, it is not easy to differentiate the stem cells into the cartilage cells, since under in vitro conditions, most differentiation-inducing promoters used to differentiate the stem cells into the cartilage cells may cause side effects in vivo. Accordingly, the present inventors have conducted various studies in order to develop a component that does not cause side effects in vivo while differentiating stem cells into cartilage cells in vivo. As a result, the present inventors confirmed that in the case of using porcine cartilage powder (PCP), the PCP does not cause side effects while differentiating stem cells into cartilage cells in vivo.

In particular, a differentiation-inducing promoter capable of differentiating stem cells into cartilage cells under in vitro conditions may not play a normal role in vivo. In fact, in the case of hyaluronic acid (HA), which is known to differentiate stem cells into cartilage cells under in vitro conditions, it was confirmed that the simultaneous administration of HA in vivo does not differentiate stem cells into cartilage cells and inhibits differentiation of normal stem cells.

However, it has been confirmed that the PCP may induce or promote the process of differentiating stem cells into cartilage cells not only in vitro but also in vivo. In addition, it has been confirmed that treatment of PCP with stem cells further promoted differentiation into cartilage cells compared to treatment of stem cells alone, thereby effectively treating arthropathy caused in vivo.

In particular, when the complex containing the PCP and the stem cells is administered to an individual suffering from arthropathy, the stem cells contained in the complex are differentiated into cartilage cells by the PCP, and stem cells existing inherently in vivo may also be differentiated into cartilage cells by the differentiated cartilage cells, thereby exhibiting a more improved therapeutic effect for arthropathy.

As described above, a method of treating arthropathy by regenerating damaged cartilage using stem cells and a cartilage cell-free crush has so far not been reported, and was developed for the first time by the present inventors.

As one embodiment for achieving the above object, the present invention provides a complex containing stem cells or a culture thereof, and a cartilage cell-free crush for promoting cartilage differentiation.

The term "stem cells" of the present invention means cells having the ability to be differentiated into various tissues, i.e., 'undifferentiated cells'.

In the present invention, the stem cells are not particularly limited as long as the stem cells may be differentiated into cartilage cells by the cartilage cell-free crush of the present invention. However, examples of the stem cells may comprise adult stem cells, pluripotent stem cells, induced pluripotent stem cells, umbilical cord blood mesenchymal stem cells (UCB-MSC), embryonic stem cells, placental stem cells, and autologous stem cells.

The multipotent stem cells are pluripotent stem cells derived from various adult cells such as bone marrow, umbilical cord blood, placenta (or placental tissue cells), and fat (or adipose tissue cells). For example, the mesenchymal stem cells derived from bone marrow have been the subject of various studies for development as cell therapeutic agents by pluripotency, which may be differentiated into adipose tissue, bone/cartilage tissue, and muscle tissue.

Meanwhile, the adult stem cells may be derived from tissues selected from the group consisting of umbilical cord, umbilical cord blood, bone marrow, fat, muscle, nerve, skin, amniotic membrane, and placenta. In addition, the adult stem cells may be mesenchymal stem cells, mesenchymal stromal cells, or multipotential stem cells, and preferably human umbilical cord blood mesenchymal stem cells (hUCB-MSC). A method of obtaining stem cells in each tissue may be performed by methods known in the art and is not limited to the method of the embodiment of the present invention.

The term "culture" of the present invention means a product obtained by culturing cells under specific conditions.

In the present invention, the culture may comprise a cell culture solution containing stem cells, a culture supernatant obtained by removing stem cells from the cell culture solution, a dilution solution thereof, and the like. The composition of the culture may further comprise not only a component required for culturing the stem cells, but also a component that acts synergistically with the stem cell proliferation. The composition of the culture may be easily selected by those skilled in the art.

As a medium used for culturing the stem cells, a general medium known to be suitable for stem cell culture in the art may be used. For example, the medium may comprise Dulbecco's modified Eagle medium (DMEM) or a keratinocyte serum-free medium (Keratinocyte-SFM).

The stem cell medium may be supplemented with additives. Generally, the additives may comprise neutral buffers (e.g., phosphates and/or high-concentration bicarbonates) and protein nutrients (e.g., serum, such as FBS, serum replacement, albumin, or essential amino acids and non-essential amino acids such as glutamine) in an isotonic solution. Furthermore, the additives may comprise lipids (fatty acid, cholesterol, or serum HDL or LDL extract) and other components found in most types of storage media thereof (e.g., insulin or transferrin, nucleoside or nucleotide, pyruvate, any ionized form or salt sugars such as glucose, selenium, glucocorticoids such as hydrocortisone, and/or reducing agents such as β-mercaptoethanol).

The term "cartilage" of the present invention means an in vivo connective tissue composed of cartilage cells and a relatively large amount of cartilage matrix. Among the muscles, cartilage, and bone, which belong to connective tissue, cartilage is more flexible than bone, and harder than muscle.

In most cartilage tissues, the cartilage cells are generally the same, but comprise different cartilage matrix depending on a position, role, and the like of the cartilage tissue. As such, depending on the cartilage matrix, cartilage is generally classified into three types of cartilage (hyaline cartilage, elastic cartilage, and fibrous cartilage). However, depending on conditions such as a site where the cartilage is formed, timing of development, a method of inducing differentiation, etc., the generated cartilage matrix may comprise different components and a composition ratio of the components.

For example, a cartilage matrix regenerated naturally by in vivo stem cells and a cartilage matrix produced by differentiating stem cells under in vitro conditions may exhibit a significant difference in the types and contents of proteins contained in these cartilage matrixes. In addition, in the case of cartilage produced by differentiating stem cells, the stem cells are generally treated with a differentiation-inducing promoter for cartilage differentiation to differentiate the stem cells into cartilage cells, and then differentiate the differentiated cartilage cells into a cartilage matrix. There is a significant difference in type and content of proteins contained in the produced cartilage matrix according to the type of differentiation-inducing promoter used at this time. As such, the cartilage matrixes containing different kinds and contents of proteins may have different roles in vivo.

In one embodiment of the present invention, it has been confirmed that a differentiation-inducing promoter capable of differentiating stem cells into cartilage cells under in vitro conditions may induce different types of cartilage differentiations in vivo. Specifically, under in vitro conditions, it has been confirmed that the porcine cartilage powder (PCP) and hyaluronic acid (HA) of the present invention may each differentiate stem cells into cartilage cells. Next, a model animal having damage to a hyaline cartilage part existing in an animal joint region was prepared, and a complex comprising PCP and stem cells or a complex comprising HA and stem cells was administered, and then therapeutic effects of these complexes on cartilage damage were compared. As a result, it has been confirmed that in the case of administering the complex comprising the PCP and the stem cells, a cartilage regeneration effect was further enhanced as compared with a case of administering the stem cells alone, while in the case of administering the complex comprising the HA and the stem cells, a cartilage regeneration effect at a relatively low level was exhibited as compared with a case of administering the stem cells alone. From the above results, it was analyzed that the PCP differentiated the stem cells into hyaline cartilage in vivo to improve regeneration of damaged hyaline cartilage, whereas the HA differentiated the stem cells into different types of cartilage other than the hyaline cartilage to inhibit the regeneration of the damaged hyaline cartilage.

The term "hyaline cartilage" of the present invention is also referred to as "glass cartilage" and refers to cartilage which has a matrix which is generally translucent tinged with blue-white in vivo, transparent, and formed into a visually uniform tissue and comprises 60% to 80% water and comprises a complex protein (mucoid) containing chondroitin sulfate and perichondrium. Cartilage cells in the structure of the hyaline cartilage are present around the cartilage matrix. The hyaline cartilage is known to constitute costal cartilage, nasal cartilage, laryngeal cartilage, articular cartilage, tracheal cartilage, etc. in vivo.

The term "elastic cartilage" of the present invention refers to cartilage which is opaque and yellow, has elastic fibers containing a net structure in a cartilage matrix, and comprises the perichondrium. The elastic cartilage is known to constitute auricular cartilage, meatus acusticus cartilage, epiglottal cartilage, and the like.

The term "fibrous cartilage" of the present invention refers to cartilage in the form in which a white fibrous tissue and a cartilage matrix are mixed at various ratios. The fibrous tissue included in the fibrous cartilage is generally composed of collagen, and usually exhibits a characteristic between those of the hyaline cartilage and the elastic cartilage, but does not include the perichondrium. The cartilage cells are present in a mixed form in the fibrous tissue, which is either free alone or forms a small population of cells. The fibrous cartilage is known to constitute intervertebral discs, cotyloid ligaments, articular meniscus, and the like in vivo.

The term "cartilage cell-free crush" of the present invention means a bio-derived material obtained by crushing a cartilage matrix in which the cartilage cells are removed from the cartilage by a known method.

In the present invention, the cartilage cell-free crush acts on stem cells to induce differentiation into cartilage cells. The function of the cartilage cell-free crush may be performed not only by the differentiation-inducing components contained in the cartilage cell-free crush, but also by physical characteristics of the cartilage cell-free crush itself. That is, since the cartilage cell-free crush is in a particular form composed of a cartilage matrix having relatively high hardness compared to cartilage cells, the particular crush additionally serves as a supporter of the stem cells to promote the differentiation of stem cells.

The cartilage cell-free crush is not particularly limited as long as the crush may induce the differentiation of stem cells into cartilage cells. However, the cartilage cell-free crush may comprise a crush obtained by mechanically crushing the cartilage matrix in which the cartilage cells are removed, repeating freezing/thawing of the cartilage matrix in which the cartilage cells are removed, or treating the cartilage matrix in which the cartilage cells are removed with ultrasonic waves; an enzyme hydrolysate obtained by treating the cartilage matrix in which the cartilage cells are removed with various enzymes (trypsin, endonuclease, exonuclease, etc.); a reaction product obtained by treating the cartilage matrix in which the cartilage cells are removed with an alkali or acidic reagent or a surfactant; and the like.

In addition, as an example, although not particularly limited thereto, the cartilage matrix may use a cartilage matrix derived from a mammal such as a pig, a cow, a rabbit, or the like, and as another example, may use a cartilage matrix derived from a pig, which is most similar to that of humans.

In one embodiment of the present invention, porcine cartilage powder (PCP), which is obtained by producing a cartilage matrix in which the cartilage cells are removed from the cartilage of the pig and then performing freeze-drying and crushing processes, was used as the cartilage cell-free crush.

The term "complex" of the present invention refers to an agent for promoting cartilage differentiation comprising the stem cells and the cartilage cell-free crush.

In the present invention, the complex comprises not only a composition in which the stem cells and the cartilage cell-free crush are mixed, but also any form of formulation comprising the stem cells and the cartilage cell-free crush such as a complex in which the stem cells and the cartilage cell-free crush are immobilized on a carrier, and a kit in which the stem cells and the cartilage cell-free crush are each packaged. Further, in addition to the formulation forms, the complex comprises all reaction products produced by reaction of the stem cells and the cartilage cell-free crush or byproducts of the reaction products, such as cartilage cells differentiated from the stem cells by the cartilage cell-free crush, a culture of the cartilage cells, a culture supernatant of the culture, an extract of the culture, and a fraction of the culture.

In addition, the complex may further comprise an agent for promoting cartilage differentiation capable of promoting the cartilage differentiation of stem cells in addition to the stem cells and the cartilage cell-free crush. The agent for promoting cartilage differentiation is not particularly limited thereto as long as the agent acts with the cartilage cell-free crush to promote the differentiation of the stem cells into the cartilage cells, but as an example, may be a bone morphogenetic protein 6 (BMP 6).

In another embodiment, the present invention provides a method of fabricating cartilage or cartilage cells using the complex. Specifically, the method for fabricating the cartilage or cartilage cells of the present invention comprises differentiating stem cells into cartilage cells in the presence of a cartilage cell-free crush.

The term "differentiation" of the present invention means a phenomenon in which a relatively simple system is generally divided into two or more qualitatively different partial systems, particularly, a phenomenon in which cells are divided and proliferated to be specified into different structures or functions during growing, that is, a phenomenon in which cells, tissues, and the like of an organism are changed into forms or functions for performing each given task. For example, the differentiation may comprise a phenomenon in which a qualitative difference occurs between parts of any biological system which have been almost homogeneous at first, or as the result, the system is divided into qualitatively distinguishable substructures or partial systems, such as a phenomenon in which the head, torso, or the like is distinguished between egg parts which were homogeneous at first in the development of an individual, or muscle cells or neurons are distinguished even in cells. Relatively, "undifferentiated" means a state comprising characteristics of stem cells which are not yet differentiated.

For the purpose of the present invention, the differentiation may be interpreted to mean a series of processes in which the stem cells are transformed into the cartilage cells by treatment of the cartilage cell-free crush.

For example, cartilage or cartilage cells may be fabricated by differentiating umbilical cord blood-derived stem cells in the presence of the porcine cartilage powder.

In order to improve the efficiency of differentiation into the cartilage cells, before the stem cells are treated with the cartilage cell-free crush of the present invention, the method may further comprise treating the agent for promoting the cartilage differentiation simultaneously with treatment or after treatment. The agent for promoting the cartilage differentiation is the same as defined above.

As yet another embodiment, the present invention provides cartilage or cartilage cells fabricated by the method.

As described above, the cartilage may comprise a cartilage matrix comprising different components and composition ratios of the components, depending on conditions such as a site where the cartilage is formed, timing of development, a method of inducing differentiation, and the like.

The cartilage or cartilage cells provided by the present invention may be fabricated by differentiating cartilage cells from stem cells in the presence of the cartilage cell-free crush, as described above. The cartilage or cartilage cells fabricated above exhibit a characteristic which is clearly distinguished from cartilage in which differentiation is induced via a conventional method. One of the characteristics is to effectively treat the cartilage damage in vivo as compared with cartilage cells in which differentiation is induced by hyaluronic acid, and the other characteristic is to differentiate the stem cells into the cartilage cells via a paracrine effect with only the fabricated cartilage or cartilage cells.

In particular, the paracrine effect exhibited by the cartilage or the cartilage cells of the present invention has thus far not been reported, and was confirmed for the first time by the present inventors.

The cartilage or the cartilage cells provided in the present invention may be fabricated by differentiating umbilical cord blood-derived stem cells in the presence of the porcine cartilage powder.

As still another embodiment, the present invention provides a pharmaceutical composition for preventing or treating arthropathy comprising the complex.

The complex provided in the present invention may not only differentiate stem cells into cartilage cells under in vitro conditions, but may also exhibit the effect of regenerating or treating damaged cartilage or cartilage cells under in vivo conditions. In addition, the complex of the present invention may regenerate not only cartilage or cartilage cells damaged by extrinsic factors such as trauma, but also cartilage or cartilage cells damaged or lost by inherent factors such as aging, genetic diseases, and immune diseases. In particular, pathological symptoms of the damage or loss of the cartilage or cartilage cells due to the inherent factors do not appear immediately, but gradually. Therefore, in the case of suppressing the damage or loss of the cartilage or cartilage cells due to the inherent factors by administering of the complex of the present invention, an effect of preventing arthropathy may be exhibited.

Accordingly, the complex of the present invention may be used as an active ingredient of the pharmaceutical composition for preventing or treating arthropathy.

The term "arthropathy" of the present invention is also referred to as "arthrosis" or "osteo-arthrosis" and refers to a disease involving analgia and dysarthrosis, and it is classified as a neurotrophic disease of the joints. Generally, arthropathy comprises polyarthrosis, coxarthrosis, gonarthrosis, spondyloarthropathy, and the like and may involve cartilage damage or cartilage dysfunction. Most types of arthropathy are known to progress to arthritis due to inflammation involved.

The term "treatment" of the present invention means any action that improves or alleviates symptoms of arthropathy by the administration of the pharmaceutical composition.

In addition, the content of cartilage cell-free crush contained in the pharmaceutical composition of the present invention is not particularly limited, and may be, as an example, 0.1 ng/mL to 100 ng/mL, as another example, 1 ng/mL to 10 ng/mL, and as yet another example, 5 ng/mL.

In addition, the content of the stem cells or the culture thereof included in the pharmaceutical composition of the present invention is not particularly limited, but may be, as an example, $1.0 \times 10^5$ to $1.0 \times 10^9$ cells, as another example, $1.0 \times 10^6$ to $1.0 \times 10^8$ cells, and as yet another example, $1.0 \times 10^7$ cells per 1 mL.

The stem cells or the culture thereof according to the present invention may be used without being frozen or may be frozen for use later. If it is required to be frozen, a standard cryopreservative (e.g., DMSO, glycerol, or Epilife cell freezing medium (Cascade Biologics)) may be added to a pre-freezing cell group.

The pharmaceutical composition of the present invention comprises, as an active ingredient, stem cells or a culture thereof and a cartilage cell-free crush, and when the pharmaceutical composition is administered to an individual suffering from arthropathy, the stem cells administered together may be primarily differentiated into the cartilage cells by the cartilage cell-free crush included in the composition, and the stem cells existing inherently in vivo may be secondarily differentiated into the cartilage cells via a paracrine effect of the primarily differentiated cartilage cells, thereby exhibiting a more improved therapeutic effect on arthropathy.

As still yet another embodiment, the present invention provides a method for preventing or treating arthropathy using the complex or the pharmaceutical composition comprising the same.

Specifically, the method for preventing or treating arthropathy comprises administering the complex or the pharmaceutical composition comprising the same to a subject which is likely to develop arthropathy or develops arthropathy.

The term "subject" of the present invention means a living organism which develops or may develop arthropathy, and as an example, may be higher vertebrate animals comprising articular tissues, and as another example, may be mammals, and as yet another example, may be primates, and as still another example, may be rats, mice, livestock, and the like, including humans.

The term "administration" of the present invention means an act of introducing a predetermined material to a patient via an appropriate method, and an active ingredient may be formulated for human or veterinary and then administered through various routes.

In the present invention, the administration may be interpreted to mean an action of introducing the complex of the present invention or the pharmaceutical composition comprising the same to a subject developing arthropathy.

The administration route of the pharmaceutical composition comprising the complex of the present invention is not particularly limited, but as an example, may be administered by a parenteral route such as an intravascular, intravenous, intraarterial, intramuscular, or subcutaneous route, and as another example, may be administered by an oral, nasal, rectal, transdermal, or aerosol inhalation route.

The stem cells or the culture thereof and the cartilage cell-free crush included in the complex of the present invention may be administered simultaneously or sequentially.

The complex of the present invention may be administered to cartilage tissue comprising the stem cells.

In addition, in order to improve the therapeutic effect of arthropathy, the method may further comprise administering an agent for promoting cartilage differentiation capable of promoting cartilage regeneration, cartilage differentiation, and the like without side effects in vivo before, during, or after administering the administration of the pharmaceutical composition of the present invention. The agent for promoting cartilage differentiation is not particularly limited, but may be a bone morphogenetic protein 6 (BMP 6) or the like.

The complex of the present invention or the pharmaceutical composition comprising the same may be administered in a pharmaceutically effective amount.

The term "pharmaceutically effective amount" of the present invention means an amount sufficient to treat diseases at a reasonable benefit/risk ratio applicable to medical treatment without causing side effects.

In addition, the pharmaceutical composition according to the present invention may be formulated and administered into a unit administration type formulation suitable for administration to the body of a patient according to a general method in a pharmaceutical field, and the formulation comprises an effective dosage by one or several administrations. A formulation suitable for the purpose preferably comprises injection agents such as an injection ampoule, infusion agents such as an infusion bag, spray agents such as an aerosol agent, and the like, as parenterally administered formulations. The injection ampoule may be mixed and prepared with an injection solution immediately before use, and the injection solution may use physiological saline, glucose, mannitol, Ringer's solution, and the like. In addition, the infusion bag may be made of polyvinyl chloride or polyethylene, and may comprise infusion bags manufactured by Baxter, Becton Dickinson, Medcep, National Hospital Products, and Terumo corporations.

The pharmaceutical agent may further comprise one or more general pharmaceutically acceptable inert carriers, for example, in the case of an injection agent, a preservative, an anhydrous agent, a solubilizer, a stabilizer, or the like, and in the case of a local administering agent, a base, an excipient, a lubricant, a preservative, or the like.

The pharmaceutical composition comprising stem cells or a culture thereof and a cartilage extract according to the present invention may be administered with an agent for treating other stem cells or other arthropathies used for transplantation and other uses by an administration method commonly used in the art or in the form of a mixture. Preferably, the pharmaceutical composition can be engrafted or transplanted directly to a disease site of a patient to be treated or transplanted or injected directly to the abdominal cavity, but is not limited thereto. In addition, the administration can use both non-surgical administration using a catheter and surgical administration such as injection or transplantation after incision of a disease site, but a non-surgical administration method using a catheter is more preferable. In addition, according to a general method, as parenteral administration, for example, transplantation by intravascular injection as a common method of hematopoietic stem cell transplantation is also possible in addition to direct administration to lesions.

A daily dosage of the stem cells included in the pharmaceutical composition may be administered with, as an example, $1.0 \times 10^{10}$ cells/kg weight, and as another example, $1.0 \times 10^5$ to $1.0 \times 10^9$ cells/kg weight once or several times. However, it should be understood that an actual dosage of the active ingredient should be determined by various relevant factors such as a disease to be treated, the severity of the disease, a route of administration, weight, age and gender of a patient, or the like. Therefore, the dosage is not limited to the scope of the present invention in any way.

As still yet another embodiment, the present invention provides a composition for inducing differentiation of cartilage cells comprising cartilage or cartilage cells differentiated from stem cells in the presence of the cartilage cell-free crush fabricated via the method.

As described above, since the cartilage or cartilage cells fabricated via the method of the present invention may differentiate the stem cells into the cartilage cells via a paracrine effect by themselves without an additional cartilage cell-free crush, the fabricated cartilage or cartilage cells may be used as an active ingredient of the composition for inducing differentiation of cartilage cells.

That is, the cartilage or cartilage cells may be co-cultured with the stem cells to differentiate the stem cells into the cartilage cells.

In addition, the cartilage or cartilage cells may be fabricated by differentiating umbilical cord blood-derived stem cells in the presence of the porcine cartilage powder.

As still yet another embodiment, the present invention provides a method for fabricating cartilage cells using the fabricated cartilage cells.

Specifically, the method for fabricating cartilage cells using the cartilage cells provided in the present invention comprises (a) differentiating first cartilage cells from first stem cells in the presence of a cartilage cell-free crush; and (b) co-culturing second stem cells with the differentiated first cartilage cells and differentiating the co-cultured second stem cells into second cartilage cells.

At this time, step (a) may be performed by differentiating umbilical cord blood-derived stem cells (first stem cells) in the presence of porcine cartilage powder.

As still yet another embodiment, the present invention provides a use of a complex for promoting cartilage differentiation comprising stem cells or a culture thereof and a cartilage cell-free crush for fabricating cartilage.

As still yet another embodiment, the present invention provides a use of a complex for promoting cartilage differentiation comprising stem cells or a culture thereof and a cartilage cell-free crush for preventing or treating arthropathy.

MODE FOR INVENTION

Hereinafter, the present invention will be described in more detail with reference to Examples. However, these Examples are only illustrative of the present invention, and the scope of the present invention is not limited to these Examples.

Example 1: Evaluation of Cartilage Differentiation Potency of Porcine Cartilage Powder (PCP)

Example 1-1: Induction of Cartilage Differentiation of Human Umbilical Cord Blood-Derived Mesenchymal Stem Cells Umbilical cord blood derived mesenchymal stem cells (UCB-MSCs) were inoculated in a KSB-3 medium (Kangstem biotech, Korea) containing 10% (v/v) FBS and 1%

(w/v) gentamycin and cultured under conditions of 37° C. and 5% (v/v) carbon dioxide.

A droplet containing 5×10⁵ cultured UCB-MSCs per 5 μL was obtained and inoculated in each well of a 48-well plate, left for 2 hours under conditions of 37° C. and 5% (v/v) carbon dioxide, and then attached to the bottom of the well.

The attached droplet was added with a cartilage differentiation induced medium (STEMPRO™ Chondrogenesis Differentiation Kit, ThermoFisher) containing porcine cartilage powder (PCP; 0.5%, 1%, or 2% (w/v)) or hyaluronic acid (HA; 0.25%, 0.5%, or 1% (w/v)) as a cartilage differentiation inducer and cultured for 7 days to differentiate the UCB-MSCs into cartilage cells. At this time, UCB-MSCs without treatment of a cartilage differentiation inducer were used as a control group, and the PCP was obtained by removing cells from porcine cartilage and then performing processes of lyophilization, crushing, and filtration of the porcine cartilage in which the cells are removed.

FIG. 1A is a micrograph showing results of evaluating a cartilage differentiation level of human umbilical cord blood-derived mesenchymal stem cells (UCB-MSCs) according to types and treatment concentrations of a cartilage differentiation inducer.

As shown in FIG. 1A, it was confirmed that pellet-shaped cartilage was formed from UCB-MSCs in the case of treating PCP as well as HA as known cartilage differentiation inducers at various concentrations.

Example 1-2: Alcian Blue Staining Analysis

In the sample of Example 1-1, the cells differentiated by treating 2% (w/v) PCP were treated with 4% paraformaldehyde (PFA) and reacted for one day to immobilize the cells. The immobilized cells were treated with 1% Alcian Blue and stained for 20 minutes, and it was confirmed whether glycosaminoglycan (GAG), which is a kind of proteoglycan as a cartilage marker, was detected in the immobilized cells (FIG. 1B).

Figure 1B:
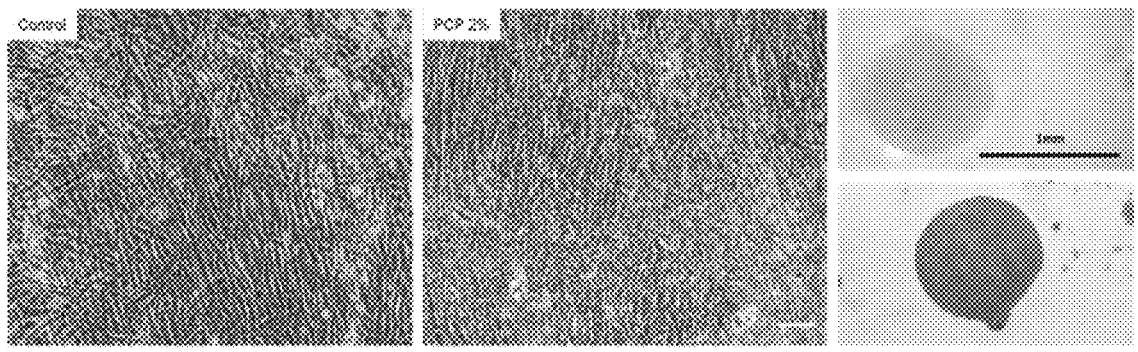
FIG. 1B is a micrograph showing results of staining cells differentiated by treating 2% (w/v) PCP with Alcian blue.

FIG. 1B is a micrograph showing results of staining cells differentiated by treating 2% (w/v) PCP with Alcian blue.

As shown in FIG. 1B, in a control group, GAG stained with Alcian blue was not detected, but in cells differentiated by treating 2% (w/v) PCP, GAG stained with Alcian blue was detected.

Example 1-3: Real-Time Polymerase Chain Reaction (RT-PCT)

Figure 1C:
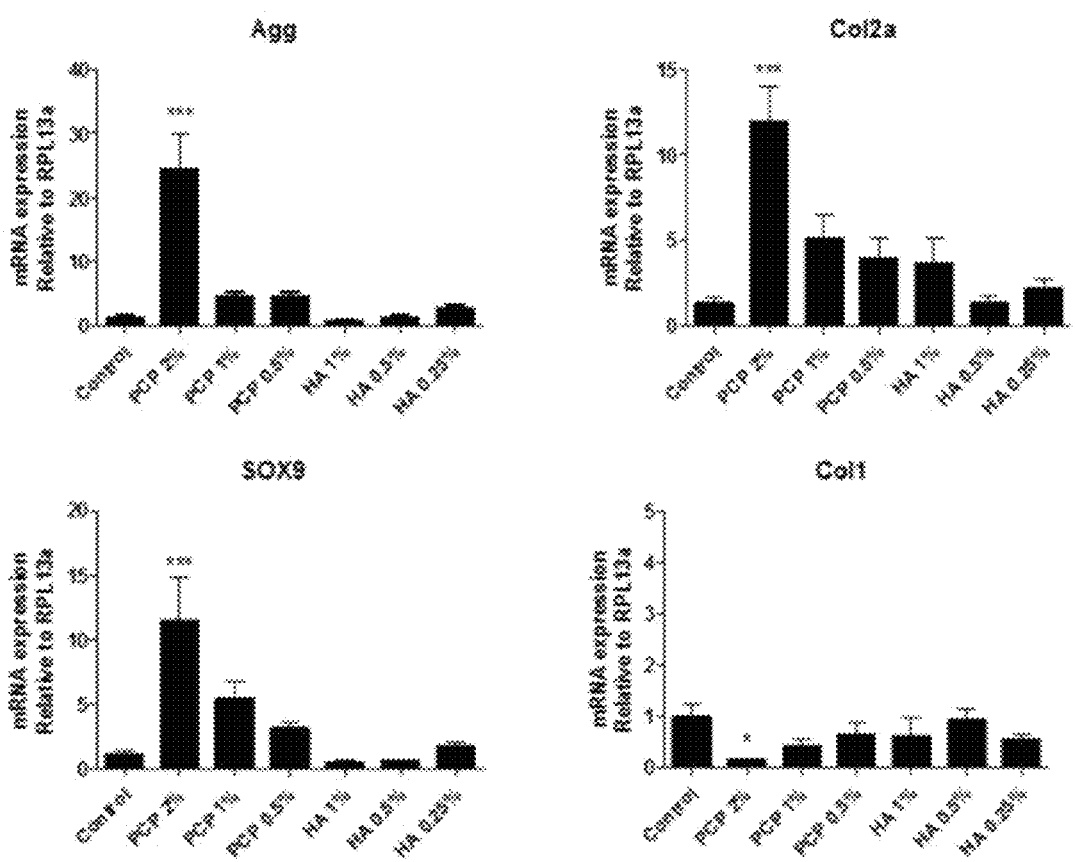
FIG. 1C is a graph showing results of comparing changes in protein expression levels according to types and treatment concentrations of a cartilage differentiation inducer in cartilage cells differentiated from UCB-MSC.

Each cell differentiated in Example 1-1 was treated with a TRIzol (Invitrogen) solution to extract total RNAs of each cell, and each cDNA was synthesized using the extracted total RNAs and AccuPower RT PreMix (Bioneer). RT-PCR was performed using the synthesized cDNAs and the following primers to compare expression levels of various proteins (aggrecan (agg), type 2 collagen (Col2a), SOX9 and type 1 collagen (Col1)) (FIG. 1C). At this time, RPL13a was used as an internal control group.

```
Aggrecan_F:
                                            (SEQ ID NO: 1)
5'-ctgcattccacgaagctaacct-3'

Aggrecan_R:
                                            (SEQ ID NO: 2)
5'-gacgcctcgccttcttgaa-3' collagen type 2 alpha 1_F:
                                            (SEQ ID NO: 3)
5'-ctactggattgacccaaccaa-3' collagen type 2 alpha 1_R:
                                            (SEQ ID NO: 4)
5'-tccatgttgcagaaaaccttca-3'

SOX9_F:
                                            (SEQ ID NO: 5)
5'-gacttctgaacgagagcgaga-3'

SOX9_R:
                                            (SEQ ID NO: 6)
5'-ccgttcttcaccgacttcctc-3' collagen type 1_F:
                                            (SEQ ID NO: 7)
5'-caggaagggccacgacaaa-3' collagen type 1_R:
                                            (SEQ ID NO: 8)
5'-ctgcggcacaagggattg-3'

RPL 13a_F:
                                            (SEQ ID NO: 9)
5'-ctatgaccaataggaagagcaacc-3'

RPL 13a_R:
                                            (SEQ ID NO: 10)
5'-gcagagtatatgaccaggtggaa-3'
```

FIG. 1C is a graph showing results of comparing changes in protein expression levels according to types and treatment concentrations of a cartilage differentiation inducer in cartilage cells differentiated from UCB-MSCs.

As shown in FIG. 1C, it was confirmed that the expression levels of aggrecan (agg), type 2 collagen (Col2a), and SOX9, which are known as cartilage marker proteins, were highest in cartilage cells differentiated by treatment with 2% (w/v) PCP, whereas the expression level of type 1 collagen (Col1), which is not a cartilage marker protein, was low in all experimental groups.

Example 1-4: Immunofluorescence Analysis

In the sample of Example 1-1, in the cells differentiated by treating 2% (w/v) PCP and the cells differentiated by treating 0.5% (w/v) HA, aggrecan (agg), and type 2 collagen (Col2a) were subjected to immunofluorescence staining.

Figure 1D:
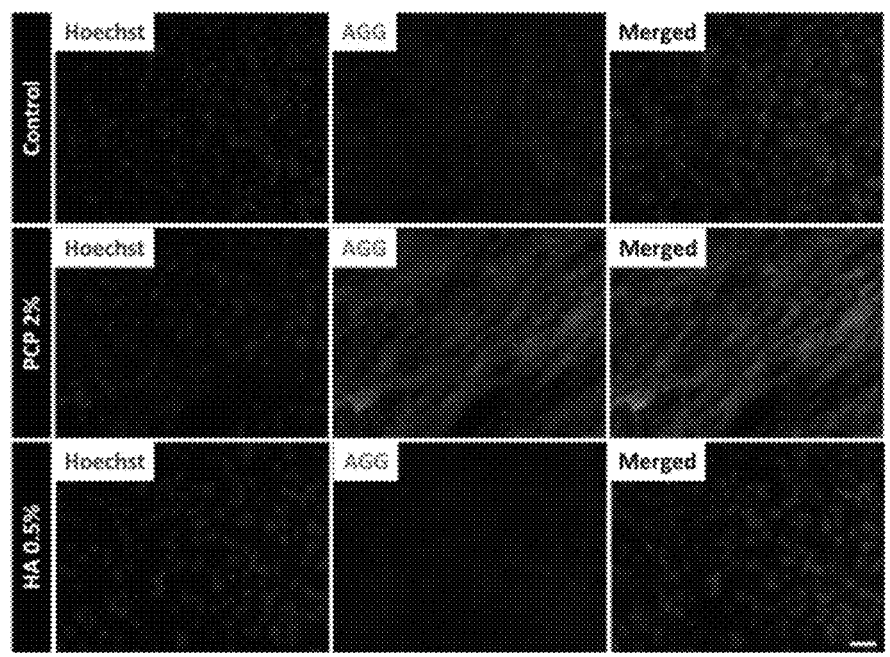
FIG. 1D is a fluorescence micrograph showing results of immunofluorescence staining for aggrecan (agg) in cells differentiated by treating 2% (w/v) PCP and cells differentiated by treating 0.5% (w/v) HA.
Figure 1E:
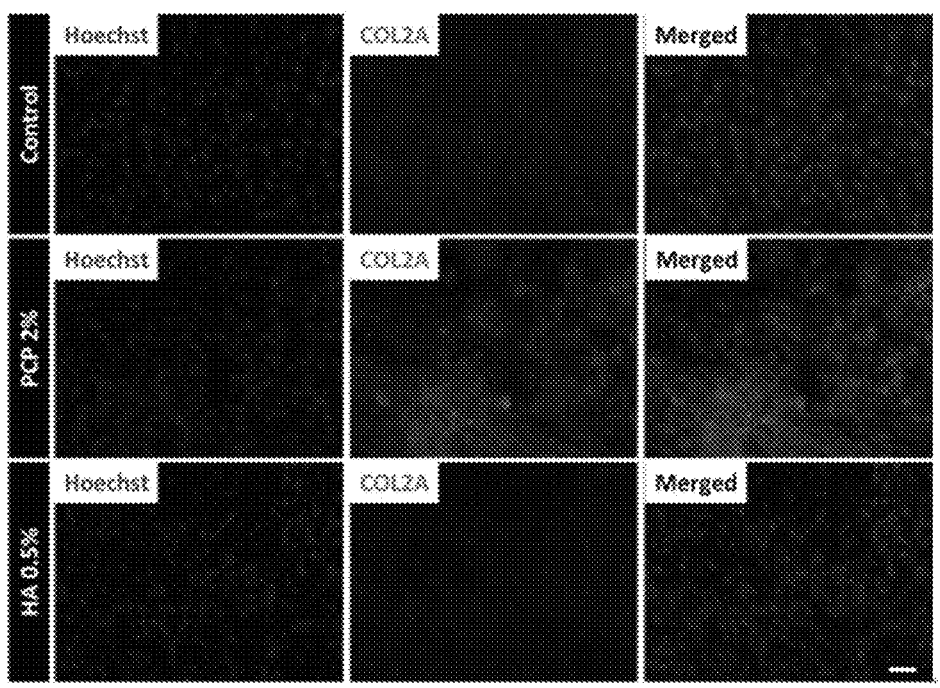
FIG. 1E is a fluorescence micrograph showing results of immunofluorescence staining for type 2 collagen (Col2a) in cells differentiated by treating 2% (w/v) PCP and cells differentiated by treating 0.5% (w/v) HA.

Approximately, the differentiated cells were immobilized and treated with 1% (w/v) BSA to be blocked, and then treated with an antibody (1:100, abcam) against aggrecan or type 2 collagen, and reacted overnight at 4° C. Next, the cells were washed with PBS, reacted with chlorine-Alexa 488-conjugated anti-mouse IgG/IgM polyclonal antibody (Invitrogen), and then observed using a fluorescence microscope (FIGS. 1D and 1E). At this time, control staining was performed using Hoechst 33342 trihydrochloride and trihydrate (Invitrogen).

FIG. 1D is a fluorescence micrograph showing results of immunofluorescence staining for aggrecan (agg) in cells differentiated by treating 2% (w/v) PCP and cells differentiated by treating 0.5% (w/v) HA, and FIG. 1E is a fluorescence micrograph showing results of immunofluorescence staining for type 2 collagen (Col2a) in cells differentiated by treating 2% (w/v) PCP and cells differentiated by treating 0.5% (w/v) HA.

As shown in FIGS. 1D and 1E, it was confirmed that in the cells differentiated by treating 2% (w/v) PCP other than the cells differentiated by treating 0.5% (w/v) HA, aggrecan, and type 2 collagen as cartilage markers were expressed at a relatively high level.

Example 1-5: Effect on Expression of BMP 6

Figure 1F:
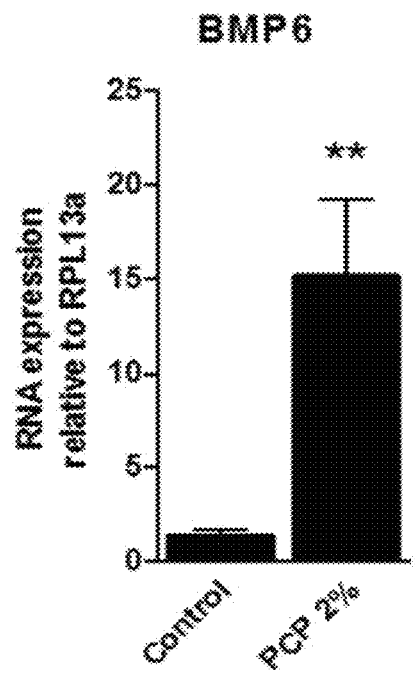
FIG. 1F is a graph showing results of measuring an expression level of BMP 6 in cells differentiated by treating 2% (w/v) PCP.

In the sample of Example 1-1, the expression level of bone morphogenetic protein 6 (BMP 6) expressed in cells differentiated by treating 2% (w/v) PCP as measured by the method of Example 1-3 using the following primers (FIG. 1F). At this time, as a control group, the expression level of BMP6 measured in cells differentiated without treating PCP was used.

```
BMP 6_F:
                                    (SEQ ID NO: 11)
5'-gctatgctgccaattactgtgatg-3'

BMP 6_R:
                                    (SEQ ID NO: 12)
5'-tgcattcatgtgtgcgttga-3'
```

FIG. 1F is a graph showing results of measuring an expression level of BMP 6 in cells differentiated by treating 2% (w/v) PCP.

As shown in FIG. 1F, it was confirmed that in the cells differentiated by treating 2% (w/v) PCP, the expression level of BMP 6 was rapidly increased.

Figure 1G:
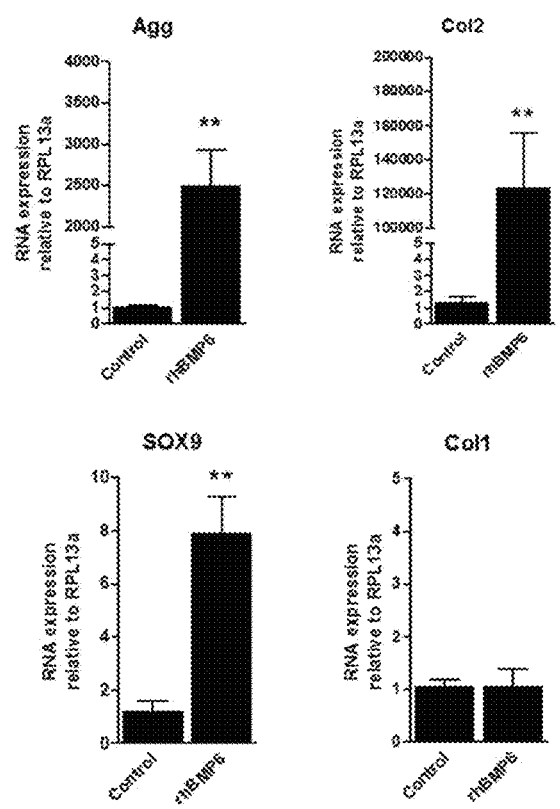
FIG. 1G is a graph showing results of comparing changes in protein expression level in cartilage cells differentiated from UCB-MSC by treating BMP 6.

In addition, the method of Example 1-1 was performed to differentiate UCB-MSCs, except that 500 ng/mL of BMP 6 was treated as a cartilage differentiation inducer, and expression levels of various proteins (aggrecan (agg), type 2 collagen (Col2a), SOX9, and type 1 collagen (Col1)) expressed in the differentiated cells obtained therefrom were compared using the method of Examples 1-3 (FIG. 1G).

FIG. 1G is a graph showing results of comparing changes in protein expression level in cartilage cells differentiated from UCB-MSC by treating BMP 6.

As shown in FIG. 1G, it was confirmed that the expression levels of aggrecan (agg), type 2 collagen (Col2a), and SOX9, which were known as cartilage marker proteins, were rapidly increased in the cartilage cells differentiated by treating BMP 6, whereas the expression level of type 1 collagen (Col1), which was not the cartilage marker protein, was not changed.

Example 1-6: Evaluation of Cytotoxicity of PCP $3 \times 10^4$ UCB-MSCs were inoculated in each well of a 24-well plate and added with PCP at various concentrations (0.5%, 1%, or 2% (w/v)), and then cultured for 3 days. After the incubation was completed, the cells were treated with 10 μL of Cell Counting Kit-8 (Dojindo) per 100μ of a culture medium and reacted for 1 hour, and then the absorbance at 450 nm was measured to confirm the cytotoxicity of PCP (FIG. 1H).

Figure 1H:
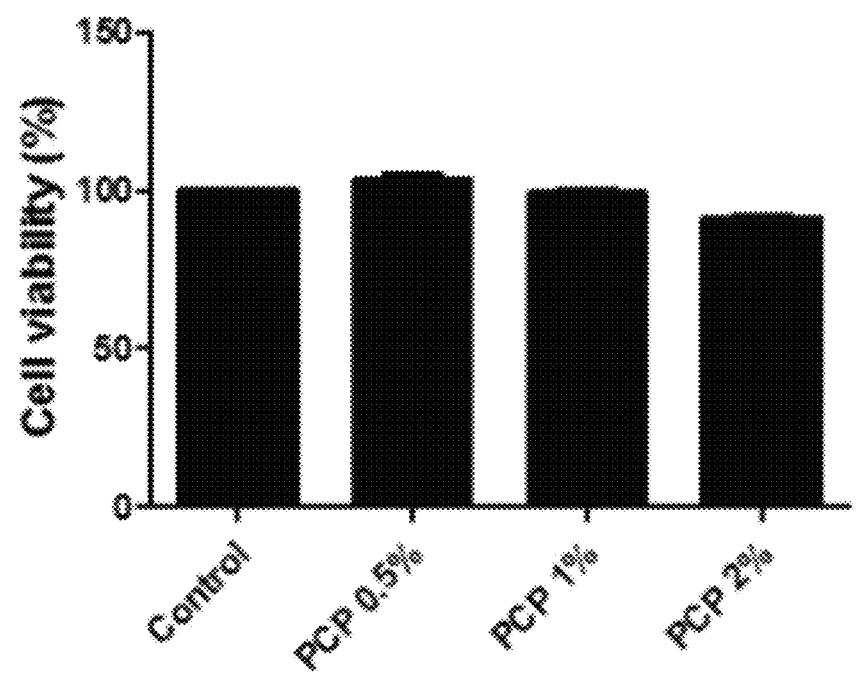
FIG. 1H is a graph showing results of comparing changes in cell viability according to a treatment concentration of PCP.

FIG. 1H is a graph showing results of comparing changes in cell viability according to a treatment concentration of PCP.

As shown in FIG. 1H, it was confirmed that even when PCP was treated at a high concentration, cell viability was not significantly affected.

When describing the results of Examples 1-1 to 1-6, it can be seen that PCP can be used as a safe cartilage differentiation inducer.

Example 2: Evaluation of UCB-MSC Differentiation Potency of Cartilage Cells Differentiated by PCP

Figure 2A:
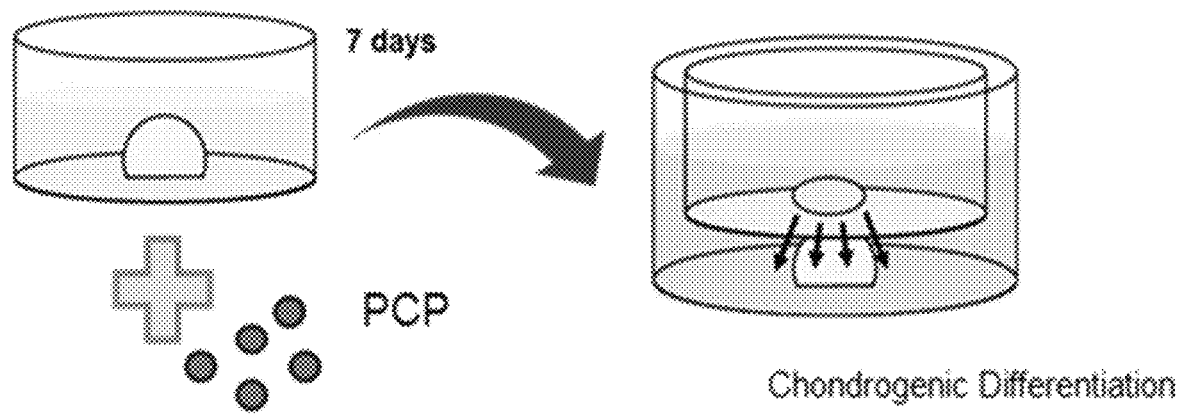
FIG. 2A is a schematic diagram showing a secondary differentiation experiment procedure of UCB-MSC using primary differentiated cartilage cells.

Example 2-1: Secondary Differentiation of UCB-MSC Using Primary Differentiated Cartilage Cells According to the method of Example 1-1, cartilage cells differentiated by treating PCP or HA with UCB-MSCs were added to an upper end insert of Transwell (Corning) equipped with a 0.4 μm polycarbonate membrane insert, and co-cultured with a droplet containing the cultured $5 \times 10^5$ UCB-MSCs per 5 μL in a cartilage differentiation-induced medium (STEMPRO™ Chondrogenesis Differentiation Kit, ThermoFisher) (FIG. 2A). As a negative control group, UCB-MSCs differentiated in a cartilage differentiation-induced medium without treating a cartilage differentiation inducer and without co-culture were used. As a positive control group, UCB-MSCs co-cultured with cells differentiated without treating a cartilage differentiation inducer were used, as experimental group 1, UCB-MSCs co-cultured with cells differentiated by treating PCP were used, and as experimental group 2, UCB-MSCs co-cultured with cells differentiated by treating HA were used.

FIG. 2A is a schematic diagram showing a secondary differentiation experiment procedure of UCB-MSC using primary differentiated cartilage cells. That is, the Transwell was divided into an upper end having an insert and a lower end having no insert, and the differentiated cells were placed at the upper end and non-differentiated UCB-MSCs were placed at the lower end, and then these cells were co-cultured.

Example 2-2: Evaluation of Differentiation Potency

Figure 2B:
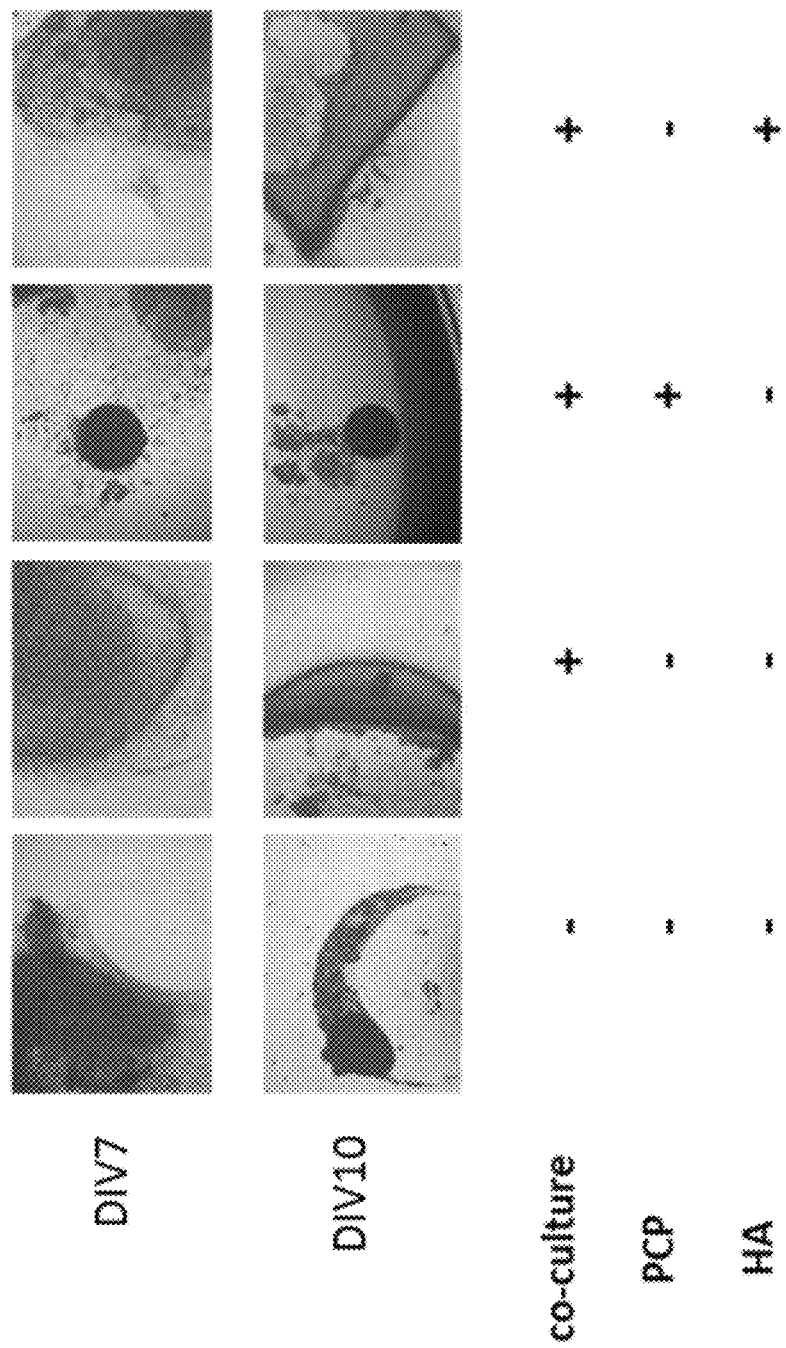
FIG. 2B is a micrograph showing results of co-culturing cartilage cells differentiated by treating PCP or HA and UCB-MSC.

The results of differentiation of UCB-MSCs co-cultured for 7 days or 10 days by the method of Example 2-1 were observed under a microscope (FIG. 2B).

FIG. 2B is a micrograph showing results of co-culturing cartilage cells differentiated by treating PCP or HA and UCB-MSC.

As shown in FIG. 2B, it was confirmed that in the case of the UCB-MSCs without co-culture (positive control group) and the UCB-MSCs (negative control group or experimental group 2) co-cultured with differentiated cells without treating PCP, UCB-MSCS were not differentiated into cartilage cells. Meanwhile, it was confirmed that in the UCB-MSCs (experimental group 1) co-cultured with the differentiated cell by treating PCP, the UCB-MSCs were differentiated into the cartilage cells.

Example 2-3: RT-PCT Analysis

Figure 2C:
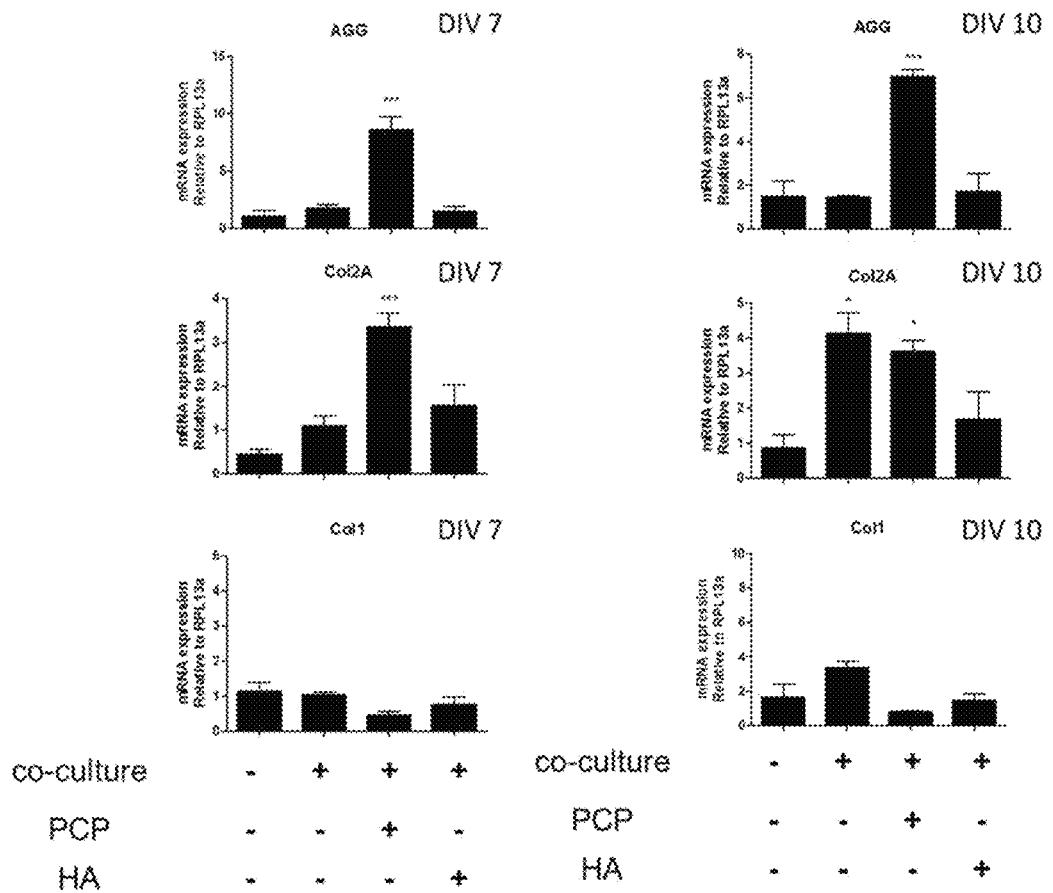
FIG. 2C is a graph showing results of comparing changes in expression level of proteins (aggrecan, type 2 collagen, and type 1 collagen) expressed in UCB-MSC co-cultured with cartilage cells differentiated by treating PCP or HA.

In UCB-MSCs co-cultured for 7 days or 10 days via the method of Example 2-1, the expression levels of aggrecan (agg) and type 2 collagen (Col2a), as expressed cartilage markers, and type 1 collagen (Col1), which was not the cartilage marker, were analyzed by the method of Example 1-3 (FIG. 2C).

FIG. 2C is a graph showing results of comparing changes in expression level of proteins (aggrecan, type 2 collagen, and type 1 collagen) expressed in UCB-MSCs co-cultured with cartilage cells differentiated by treating PCP or HA.

As shown in FIG. 2C, it was confirmed that in the UCB-MSCs co-cultured for 7 days, the expression levels of aggrecan and type 2 collagen as cartilage markers were high in the UCB-MSCs (experimental group 1) co-cultured with the differentiated cell by treating PCP.

On the other hand, it was confirmed that in the case of the UCB-MSCs without co-culture (positive control group) and the UCB-MSCs (negative control group or experimental group 2) co-cultured with differentiated cells without treating PCP, the expression levels of aggrecan and type 2 collagen were almost all low.

In addition, it was confirmed that the expression level of the type 1 collagen (Col1), which was not a cartilage marker, was generally low in all cases.

As shown in the results of Examples 2-1 to 2-3, the induction of differentiation of UCB-MSCs by the paracrine effect of the differentiated cartilage cells was only shown only in the differentiated cartilage cells treated with PCP. As a result, it was found that the differentiated cartilage cells had different characteristics according to a type of differentiation-inducing promoter, and the differentiated cartilage cells were not the same as one another.

Example 3: Analysis of Cartilage Damage Therapeutic Effect Using PCP and Stem Cells In Vivo Example 3-1: Analysis Using Cartilage Defect Model Animal Example 3-1-1: Fabrication of Cartilage Defect Model Animal Zoletil 50 (Virbac, 15 mg/kg) and rompum (Bayer, 5 mg/kg) were injected intramuscularly into male New Zealand White (NZW) rabbits to undergo general anesthesia. The fur around the right knee was removed, the medial skin of the knee joint was incised, the fascia and the articular capsule were incised, and the knee bone was bent outward to expose the articular capsule. A cartilage defect area having a diameter of 5 mm and a depth of 2 mm was made in the internal part of the femur (the middle of the knee joint furrow) using a drill bit having a diameter of 1 mm, the cartilage in the defect area was fully removed by a curette, and then the articular capsule was sutured. For 3 days after surgery, antibiotics Foxolin (Samjin Pharmaceutical, 10 mg/kg) and analgesic Maritrol (Cheil Pharmaceutical, 3 mg/kg) were injected intramuscularly twice daily, and thereafter, Foxolin was additionally treated once daily for 3 days to fabricate an articular cartilage defect (ACD) model animal.

Example 3-1-2: Therapeutic Effect of PCP and Stem Cells on Cartilage Defect Model Animal After 30 minutes from cartilage removal from the cartilage defect model animal prepared in Example 3-1-1, UCB-MSCs (experimental group 11), UCB-MSCs/PCP (experimental group 12), or UCB-MSCs/HA (experimental group 13) diluted with PBS were administered intraarticularly in a volume of 0.2 mL per rabbit, and the rabbits were raised for 4 weeks.

After cutting the articular surface to include the damaged sites of the outer femur and the femoral condyle of the articular joint of the raised model animal, changes in the cartilage defect area, the surface state of the cartilage defect area, visual observation of continuity of a defect boundary site and a newly formed tissue, and the degree of cartilage regeneration through photographing were scored and analyzed according to the International Cartilage Repair Society (ICRS) scoring system.

Figure 3A:
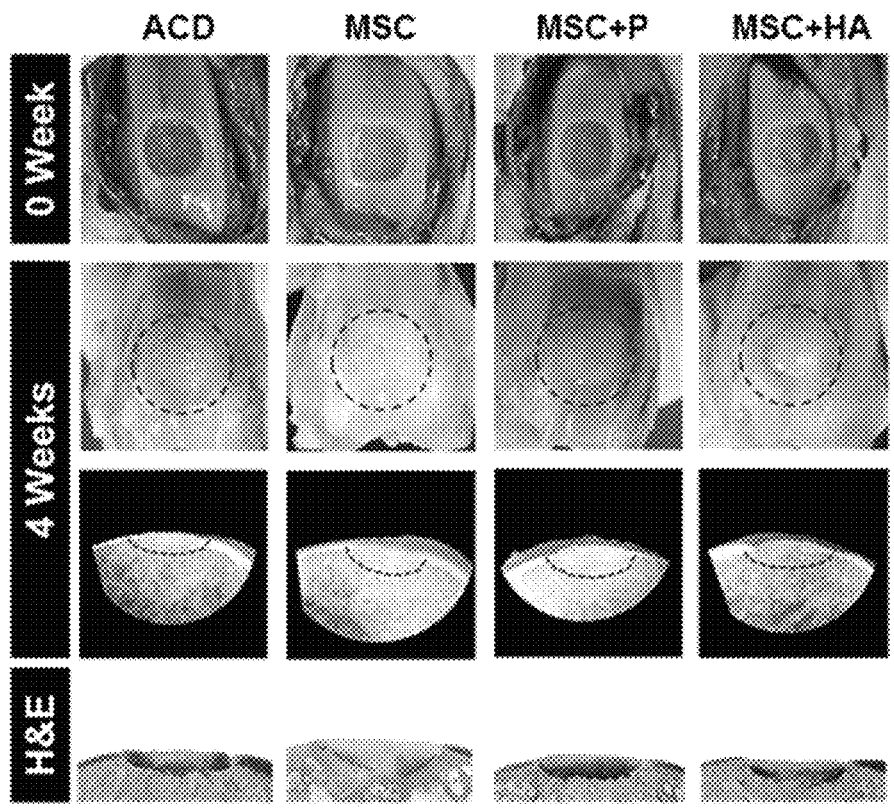
FIG. 3A is a photograph showing results of comparing cartilage recovery levels according to a combination treatment of UCB-MSC and a cartilage differentiation inducer in a cartilage defect model animal.
Figure 3B:
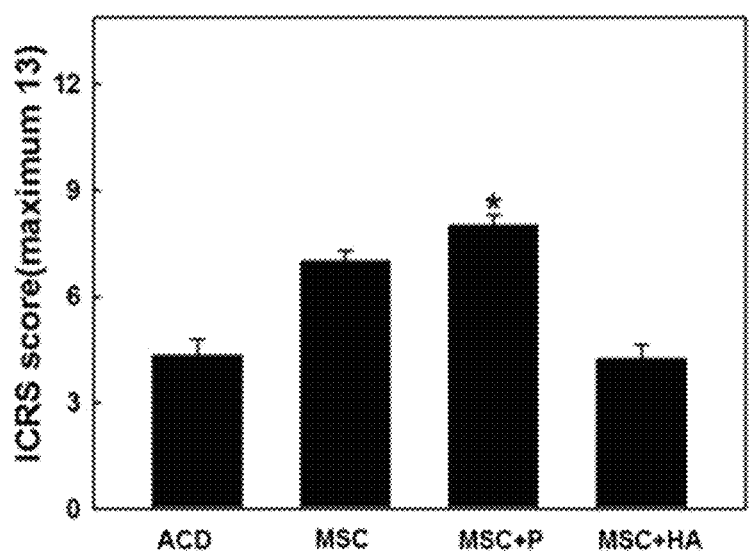
FIG. 3B is a photograph showing results of quantitative analysis of a cartilage regeneration area according to a combination treatment of UCB-MSC and a cartilage differentiation inducer in a cartilage defect model animal.

Approximately, the articular tissue was fixed in a 10% neutral formalin solution for 3 days, and then thoroughly demineralized with a 10% EDTA (pH 8.0) solution, and paraffin sections were fabricated. The tissue sections were subjected to hematoxylin & eosin (H&E) staining, a ratio of [cartilage regeneration site/width of cutting surface] was analyzed with a microscopic image analysis program Image J 4.8 v (Wayne Rasband, National Institute of Health, UAS), and a cartilage regeneration area was quantified by the ICRS score (FIGS. 3A and 3B). At this time, as a control group, a cartilage defect model animal which was not treated was used.

FIG. 3A is a photograph showing results of comparing cartilage recovery levels according to a combination treatment of UCB-MSCs and a cartilage differentiation inducer in a cartilage defect model animal.

As shown in FIG. 3A, the cartilage recovery level of the control group was measured as 90.48±0.9% of the defect area, the cartilage recovery level of experimental group 11 was measured as 91.82±0.8% of the defect area, the cartilage recovery level of experimental group 12 was measured as 94.41±5.58% of the defect area, and the cartilage recovery level of experimental group 13 was measured as 90.51±3.36% of the defect area.

FIG. 3B is a photograph showing results of quantifying a cartilage regeneration area by ICRS scores according to a combination treatment of UCB-MSCs and a cartilage differentiation inducer in a cartilage defect model animal.

As shown in FIG. 3B, it was confirmed that the ICRS score of the control group was 4.3±0.9, the ICRS score of experimental group 11 was 7.0±0.87, the ICRS score of experimental group 12 was 8.0±0.83, and the ICRS score of experimental group 13 was 4.3±0.78.

From the results of FIGS. 3A and 3B, it can be seen that in the case of combined treatment of UCB-MSCs and PCP in the cartilage defect model animal, the cartilage recovery level was highest, and as compared with the case of combined treatment of UCB-MSCs and HA in the cartilage defect model animal, in the case of treating UCB-MSCs alone, the cartilage recovery level was relatively high.

Example 3-1-3: Safranin-O Staining Analysis

The cartilage defect area was extracted from the cartilage defect model animal raised for 4 weeks in Example 3-1-2. Safranin-O staining was performed to confirm the content of proteoglycan contained in the extracted cartilage defect area (FIG. 3C).

Figure 3C:
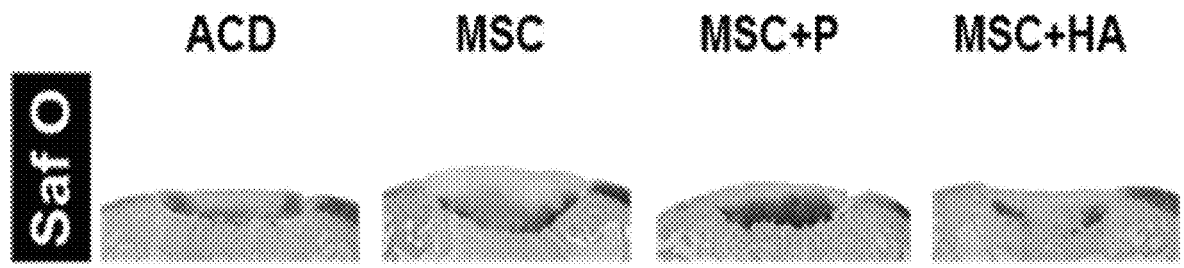
FIG. 3C is a micrograph showing results of performing safranin-O staining for analyzing proteoglycan contents in cartilage defect areas in a combination treatment of UCB-MSC and a cartilage differentiation inducer in a cartilage defect model animal.

FIG. 3C is a micrograph showing results of performing safranin-O staining for analyzing proteoglycan contents in cartilage defect areas in a combination treatment of UCB-MSCs and a cartilage differentiation inducer in a cartilage defect model animal.

As shown in FIG. 3C, the proteoglycan content in the cartilage defect area was highest in the case of UCB-MSCs and PCP (experimental group 12) in the cartilage defect model animal. In addition, it was confirmed that as compared with the combined treatment of UCB-MSCs and PCP in the cartilage defect model animal, in the case of treating UCB-MSCs alone (experimental group 11), the proteoglycan content in the cartilage defect area was relatively high.

Example 3-1-4: Immunofluorescence Staining Analysis

Figure 3D:
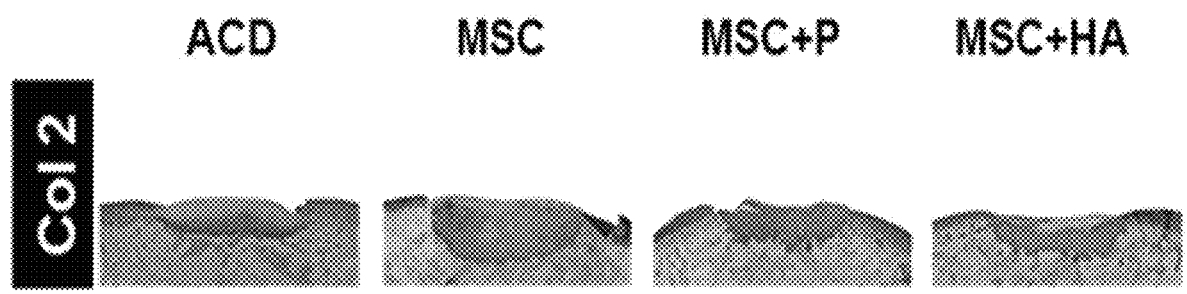
FIG. 3D is a fluorescence micrograph showing results of performing immunofluorescence staining for analyzing expression levels of type 2 collagen in cartilage defect areas in a combination treatment of UCB-MSC and a cartilage differentiation inducer in a cartilage defect model animal.

Immunostaining for type 2 collagen was performed by performing the method of Example 1-4 on the cartilage defect area extracted in Example 3-1-3 (FIG. 3D).

FIG. 3D is a fluorescence micrograph showing results of performing immunofluorescence staining for analyzing expression levels of type 2 collagen in cartilage defect areas in a combination treatment of UCB-MSCs and a cartilage differentiation inducer in a cartilage defect model animal.

As shown in FIG. 3D, the expression level of type 2 collagen in the cartilage defect area was highest in the case of combined treatment of UCB-MSCs and PCP (experimental group 12) in the cartilage defect model animal. In addition, it was confirmed that as compared with the combined treatment of UCB-MSCs and HA in the cartilage defect model animal (experimental group 13), in the case of treating UCB-MSCs alone (experimental group 11), the expression level of type 2 collagen in the cartilage defect area was relatively high.

Example 3-1-5: Alcian Blue Staining Analysis

Figure 3E:
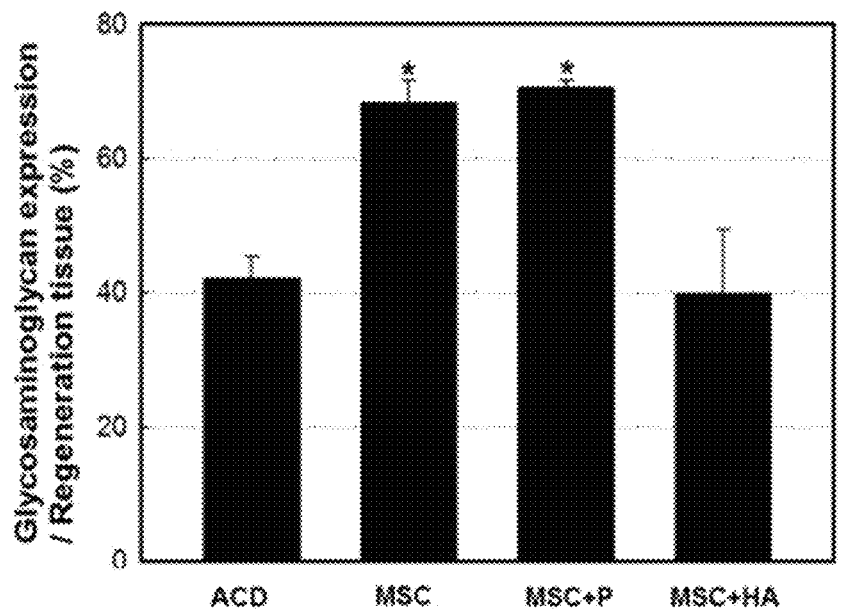
FIG. 3E is a graph showing results of performing Alcian blue staining for analyzing levels of glycosaminoglycan in cartilage defect areas in a combination treatment of UCB-MSC and a cartilage differentiation inducer in a cartilage defect model animal.

Alcian blue staining was performed to confirm the glycosaminoglycan level by performing the method of Example 1-2 on the cartilage defect area extracted in Example 3-1-3 (FIG. 3E).

FIG. 3E is a graph showing results of performing Alcian blue staining for analyzing levels of glycosaminoglycan in cartilage defect areas in a combination treatment of UCB-MSCs and a cartilage differentiation inducer in a cartilage defect model animal.

As shown in FIG. 3E, it was confirmed that in the case of the combined treatment of UCB-MSCs and PCP (experimental group 12) in the cartilage defect model animal, the glycosaminoglycan level in the cartilage defect area was highest, and even in the case of treating UCB-MSCs alone (experimental group 11), the glycosaminoglycan level was similar to that of experimental group 12.

Meanwhile, in the case of the combined treatment of UCB-MSCs and HA in the cartilage defect model animal (experimental group 13), the glycosaminoglycan level in the cartilage defect area was similar to that of the control group.

In the results of Examples 3-1-1 to 3-1-5, it was found that in the cartilage defect model animal, the combined treatment of UCB-MSCs and PCP exhibited an effect of effectively treating the cartilage damage, whereas the combined treatment of UCB-MSCs and HA did not significantly affect the cartilage damage treatment.

Example 3-2: Analysis Using Osteoarthritis Model Animal

Example 3-2-1: Fabrication of Osteoarthritis Model Animal

Male New Zealand white rabbits were subjected to general anesthesia, the medial skin of the knee joint was incised, the fascia and the articular capsule were incised, and then the knee bone was bent outward to expose the anterior cruciate ligament. The medial parenchyma of the anterior cruciate ligament and the meniscal ligament were completely cut with a surgical blade and the articular capsule was sutured. After the surgery, antibiotics and analgesics were prescribed in the same manner as before, and an osteoarthritis model (ACLT-OA) animal was fabricated.

Example 3-2-2: Therapeutic Effect of PCP and Stem Cells on Osteoarthritis Model Animal The osteoarthritis model animal fabricated in Example 3-2-1 was raised for 8 weeks, and then X-ray examination was performed to confirm the occurrence of osteoarthritis. Approximately, the right knee joint was corrected to a cranio-caudal (CC) view by general anesthesia and a radiograph was taken by X-ray (Genoray). As a result, the narrowed joint space and bone deformation at the medial tibia were scored (KL grade; Kellgren-Lawrence score system) to evaluate the degree of progression of osteoarthritis.

Figure 4A:
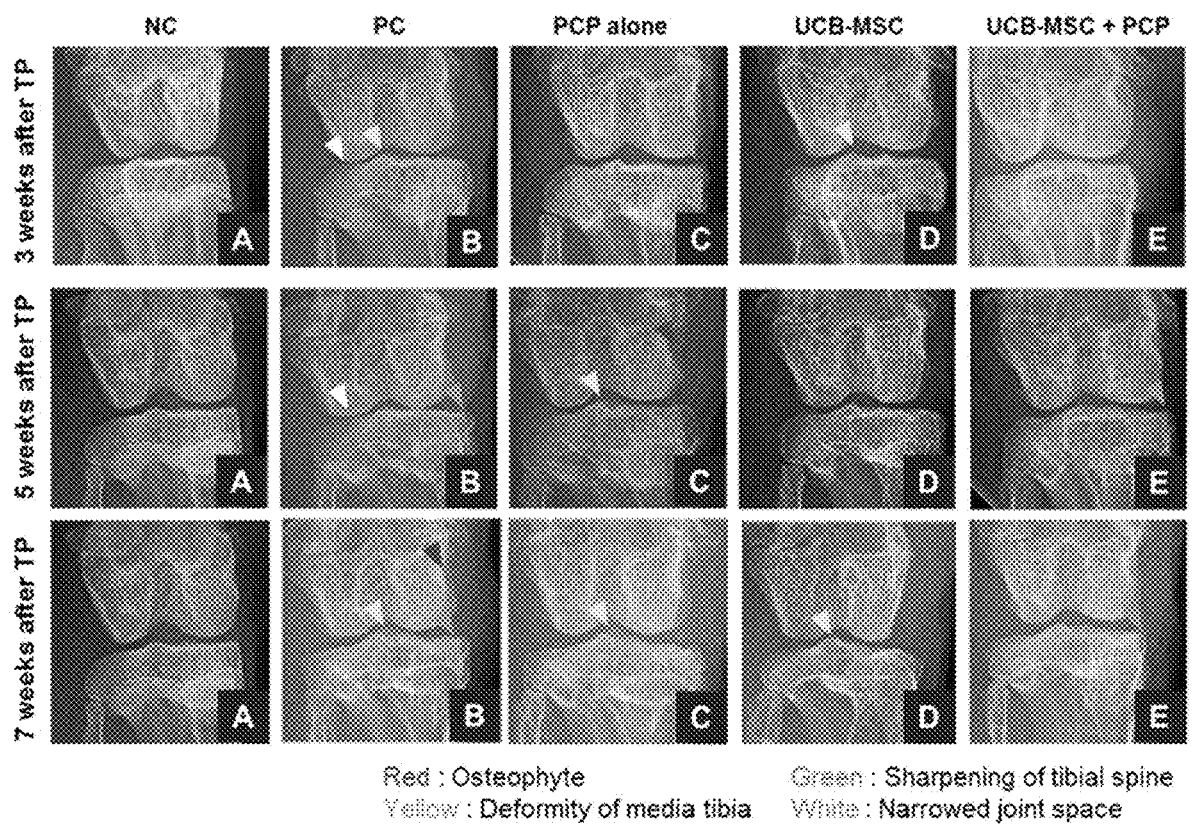
FIG. 4A is an X-ray photograph imaging an arthritis improvement effect over time according to an individual treatment or a combination treatment of UCB-MSC and PCP in an osteoarthritis model animal.

The articular cavity of the animal with the determined grade of osteoarthritis was administered with a positive control group (PC) treated with PBS, PCP diluted with PBS (experimental group 21), UCB-MSCs (experimental group 22), or UCB-MSCs/PCP (experimental group 23) as a therapeutic candidate material in a amount of 0.2 mL per rabbit, taken by X-ray at 3, 5, and 7 weeks, and scored (KL grade), and thus the degree of progression of osteoarthritis was evaluated (FIG. 4A). At this time, an animal which did not cause osteoarthritis was used as a negative control group (NC).

FIG. 4A is an X-ray photograph imaging an arthritis improvement effect over time according to an individual treatment or a combination treatment of UCB-MSCs and PCP in an osteoarthritis model animal.

As shown in FIG. 4A, in the positive control group (PC), the KL score was maintained at a constant level over time (3 weeks: 4.00, 5 weeks: 3.67, and 7 weeks: 4.00), whereas in a PCP-only administration group (experimental group 21; 3 weeks: 3.25, 5 weeks: 3.50, and 7 weeks: 3.63), in a UCB-MSCs-only administration group (experimental group 22; 3 weeks: 5.71, 5 weeks: 3.50, and 7 weeks: 3.38), and a UCB-MSCs/PCP-combined administration group (experimental group 23; 3 weeks: 2.75, 5 weeks: 2.88, and 7 weeks: 3.13), the osteoarthritis tended to be improved.

In particular, it was confirmed that in the UCB-MSCs/PCP-combined administration group, the effect of improving osteoarthritis was more increased than that of the UCB-MSCs-only administration group.

Example 3-2-3: Behavioral Evaluation

Immediately after the induction of osteoarthritis prepared in Example 3-2-2 and after 3, 5, or 7 weeks of treating the therapeutic candidate material, each model animal was allowed to freely walk in a wide space to perform a behavioral test according to arthritis induction. As a result, walk, gait, posture, weight bearing, and activity were scored, and the degree of progression of arthritis was evaluated comprehensively with the KL grade (FIG. 4B).

Figure 4B:
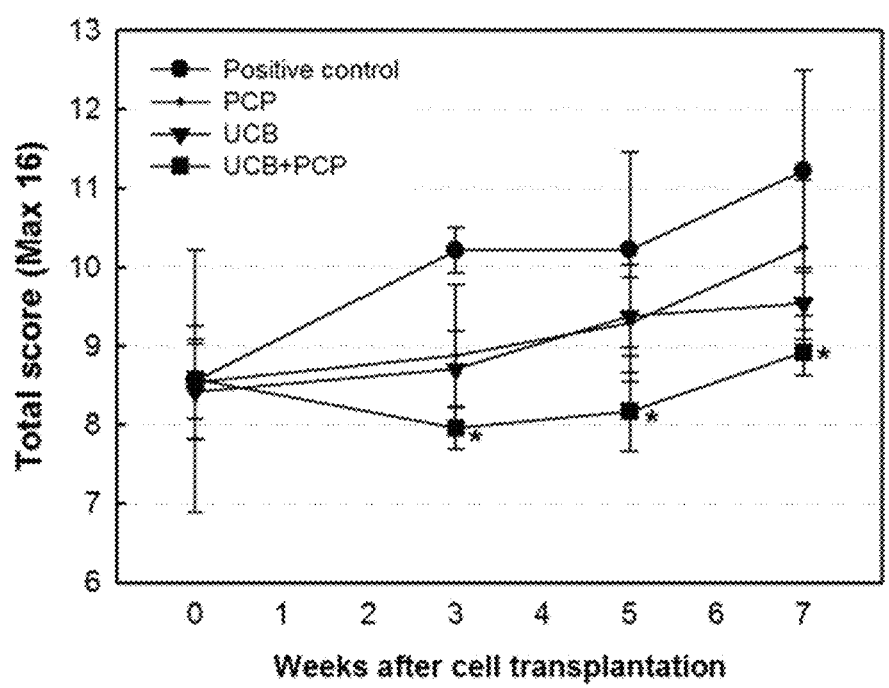
FIG. 4B is a graph showing behavioral test results according to an individual treatment or a combination treatment of UCB-MSC and PCP in an osteoarthritis model animal.

FIG. 4B is a graph showing behavioral test results according to an individual treatment or a combination treatment of UCB-MSCs and PCP in an osteoarthritis model animal.

As shown in FIG. 4B, it was confirmed that in a non-treated group (positive control group), the osteoarthritis symptoms were continuously deteriorated over time (3 weeks-10.22; 5 weeks-10.22; 7 weeks-11.22), whereas in a PCP-only treatment group (experimental group 21; 3 weeks-8.87; 5 weeks-9.29; 7 weeks-10.26), a UCB-MSCs-only treatment group (experimental group 22; 3 weeks-8.71; 5 weeks-9.21; 7 weeks-9.55), and a UCB-MSCs/PCP-combined treatment group (experimental group 23; 3 weeks-7.96; 5 weeks-8.17; 7 weeks-8.92), the osteoarthritis symptoms were improved.

In particular, it was confirmed that in the UCB-MSCs/PCP-combined treatment group (experimental group 23), the effect of improving osteoarthritis was better than that of the PCP-only treatment group (experimental group 21) or the UCB-MSCs-only treatment group (experimental group 22).

Example 3-2-4: Evaluation of Cytokine Level

Like Example 3-2-2, after 8 weeks from the administration of each therapeutic candidate material, the rabbits were anesthetized, and then physiological saline (0.1 mL) was injected into the articular cavity of the right arthritis induction site and the articular cavity fluid was collected through two repetitions. The articular cavity fluid was treated with collagenase (400 μg/mL) and hyaluronidase (40 U/mL) at 37° C. for 10 minutes and then levels of TNF-α, which is an inflammatory cytokine, were quantified by an enzyme-linked immunosorbent assay (ELISA) of TNF-α (R&D system) (FIG. 4C).

Figure 4C:
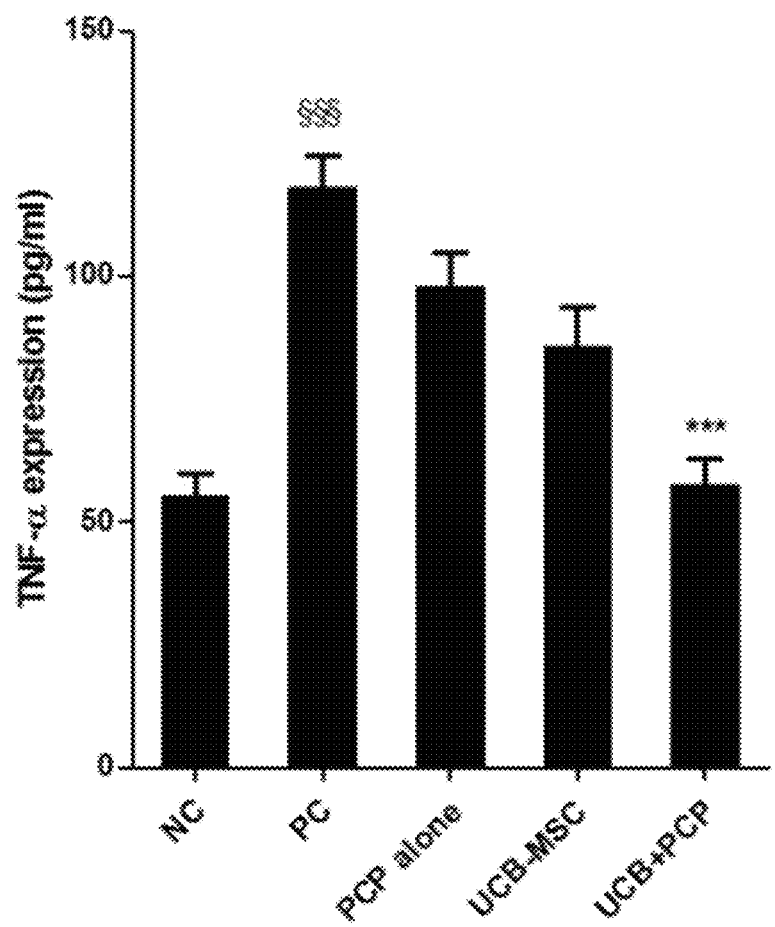
FIG. 4C is a graph showing results of comparing levels of TNF-α in an articular cavity fluid according to an individual treatment or a combination treatment of UCB-MSC and PCP in an osteoarthritis model animal.

FIG. 4C is a graph showing results of comparing levels of TNF-α in an articular cavity fluid according to an individual treatment or a combination treatment of UCB-MSCs and PCP in an osteoarthritis model animal.

As shown in FIG. 4C, it was confirmed that the levels of TNF-α in the articular cavity fluid of an osteoarthritis-induced model animal (PC) were significantly increased compared with a non-osteoarthritis-induced animal (NC), but as PCP (experimental group 21), UCB-MSCs (experimental group 22), or UCB-MSCs/PCP (experimental group 23) were administered, the levels of TNF-α in the articular cavity fluid were reduced.

In particular, it was confirmed that in the UCB-MSCs/PCP-combined treatment group (experimental group 23), the level of TNF-α in the articular cavity fluid was decreased as compared with the PCP-only treatment group (experimental group 21) or the UCB-MSC-only treatment group (experimental group 22).

Example 3-2-5: Histological Evaluation

As shown in Example 3-2-2, after 8 weeks from administration of each therapeutic candidate material, the model animals were sacrificed and the knee joint was exposed by a medial articular approach method, and a soft tissue around the knee joint was removed while being careful to avoid cartilage damage, and the supracondylar of the femur including the arthritis-induced area was extracted. Next, the femoral condyle and the tibial plateau of the knee joint were photographed (FIG. 4D), and the erosion of the articular surface, surface change, osteophyte, and hypertrophy of the femur were comprehensively quantitatively analyzed (FIG. 4E).

Figure 4D:
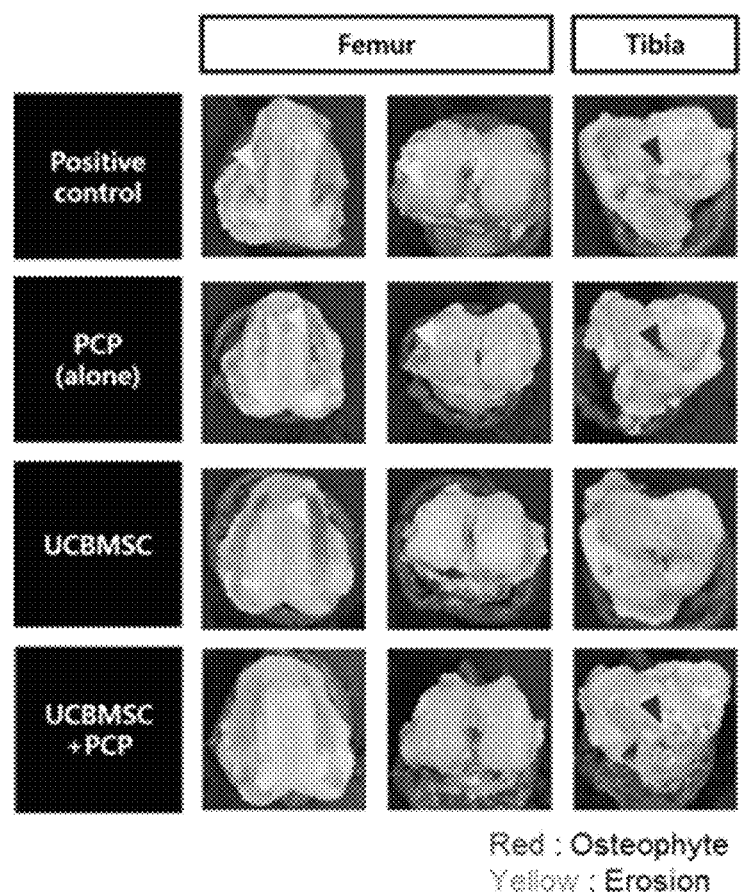
FIG. 4D is a photograph imaging femoral condyle and tibial plateau regions of the knee joint according to an individual treatment or a combination treatment of UCB-MSC and PCP in an osteoarthritis model animal.
Figure 4E:
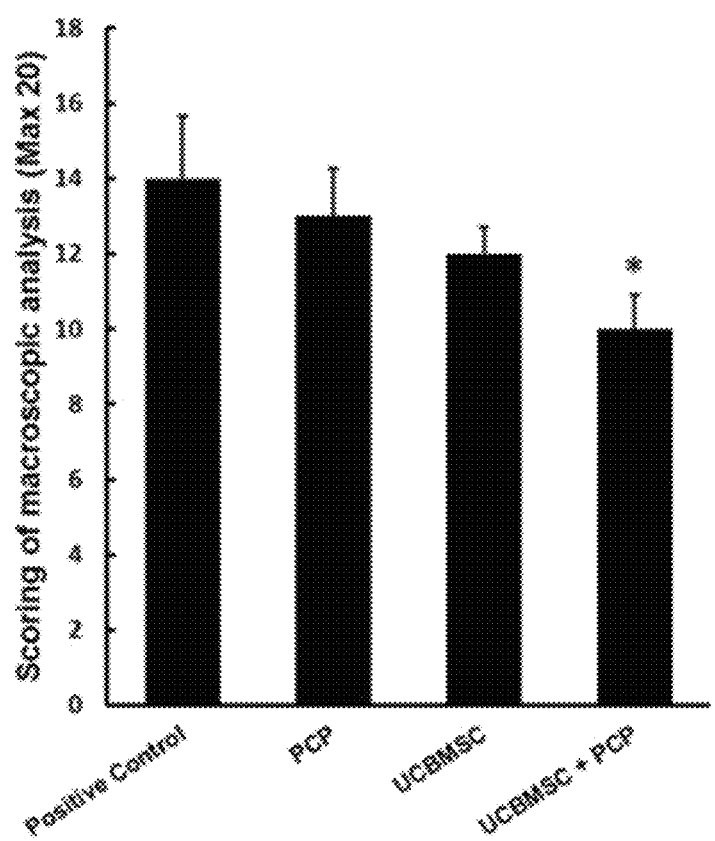
FIG. 4E is a graph showing results of comprehensive quantitative analysis of erosion of an articular surface, a surface change, osteophyte, and a hypertrophy level with the femur according to an individual treatment or a combination treatment of UCB-MSC and PCP in an osteoarthritis model animal.

FIG. 4D is a photograph imaging femoral condyle and tibial plateau regions of the knee joint according to an individual treatment or a combination treatment of UCB-MSCs and PCP in an osteoarthritis model animal, and FIG. 4E is a graph showing results of comprehensive quantitative analysis of erosion of an articular surface, a surface change, osteophyte, and a hypertrophy level with the femur according to an individual treatment or a combination treatment of UCB-MSCs and PCP in an osteoarthritis model animal.

As shown in FIG. 4D, it was confirmed that in the positive control group and the PCP-only treatment group (experimental group 21), the severe damage and erosion of the femur and the osteophyte were shown, whereas in the UCB-MSCs-only treatment group (experimental group 22) and the UCB-MSCs/PCP-combined treatment group (experimental group 23), the severe damage with the femur and the osteophyte were shown.

As shown in FIG. 4E, as results of quantifying the damage level of the femur and the osteophyte level, it was confirmed that the control group had a damage degree of $14.00\pm1.67$, experimental group 21 had a damage degree of $13.00\pm1.26$, experimental group 22 had a damage degree of $12.00\pm0.72$, and experimental group 23 had a damage degree of $10.00\pm0.92$.

As the results of Examples 3-2-1 to 3-2-5, it was confirmed that in the osteoarthritis model animal, the osteoarthritis may be improved by individually treating PCP and UCB-MSCs, and the UCB-MSCs-only treatment has a better osteoarthritis improvement effect than the PCP-only treatment. However, it was confirmed that as compared with the PCP and UCB-MSCs individual treatments, in the case of the PCP and UCB-MSCs-combined treatment, the osteoarthritis therapeutic effect was relatively high.

As a result, in order to treat the damaged cartilage in the animal with damaged cartilage, HA, as a kind of cartilage differentiation inducer, did not show any effect, but PCP also showed a therapeutic effect individually; further, it is preferable to use the PCP and the stem cells in combination, rather than using the PCP individually.

As described above, those skilled in the art will be able to understand that the present invention can be easily executed in other detailed forms without changing the technical spirit or an essential feature thereof. Therefore, it should be appreciated that the aforementioned embodiments are illustrative in all aspects and are not restricted. The scope of the present invention is represented by claims to be described below rather than the detailed description, and it is to be interpreted that the meaning and scope of the claims and all changes or modified forms derived from the equivalents thereof come within the scope of the present invention.

The invention claimed is:

1. A method for improving or treating arthropathy comprising administering by injection a complex for promoting cartilage differentiation comprising stem cells or a culture thereof and a cartilage cell-free crush or a pharmaceutical composition comprising the same to a subject in need thereof,
   wherein the complex for promoting cartilage differentiation or the pharmaceutical composition is formulated for administration intraarticularly or into a joint cavity,
   wherein the arthropathy involves degeneration or damage of cartilage,
   wherein the stem cells or the culture thereof are administered without being differentiated,
   wherein the stem cells or the culture thereof are co-administered in a state not attached to the cartilage cell-free crush,
   wherein the cartilage cell-free crush is porcine cartilage powder, and
   wherein the porcine cartilage powder is provided in an injection solution,
   wherein there are no side effects while differentiating stem cells into hyaline cartilage in vivo,
   wherein the stem cells or their cultures are differentiated into chondrocytes by porcine cartilage powder after administration,
   wherein the stem cells are umbilical cord blood-derived mesenchymal stem cells, and
   wherein the pharmaceutical composition is administered in the form of an injection.

2. The method for improving or treating arthropathy of claim 1, wherein the arthropathy comprises polyarthrosis, coxarthrosis, gonarthrosis, osteoarthritis, spondyloarthropathy.

3. The method for improving or treating arthropathy of claim 1, wherein the complex or the pharmaceutical composition further comprises an agent for promoting cartilage differentiation.

4. The method for improving or treating arthropathy of claim 1, wherein the complex for promoting cartilage differentiation or the pharmaceutical composition is administered to a cartilage tissue, in the site of administration of which stem cells reside.

5. The method for improving or treating arthropathy of claim 1, further comprising:
   administering an agent for promoting cartilage differentiation before, during, or after administering the complex for promoting cartilage differentiation or the pharmaceutical composition.

\* \* \* \* \*